(12) United States Patent
Belongia

(10) Patent No.: US 10,524,311 B2
(45) Date of Patent: Dec. 31, 2019

(54) WAX WARMERS

(71) Applicant: S. C. Johnson & Son, Inc., Racine, WI (US)

(72) Inventor: David C. Belongia, Green Valley, AZ (US)

(73) Assignee: S.C. Johnson & Son, Inc., Racine, WI (US)

(*) Notice: Subject to any disclaimer, the term of this patent is extended or adjusted under 35 U.S.C. 154(b) by 341 days.

(21) Appl. No.: 15/502,881

(22) PCT Filed: Aug. 13, 2015

(86) PCT No.: PCT/US2015/045045
§ 371 (c)(1),
(2) Date: Feb. 9, 2017

(87) PCT Pub. No.: WO2016/025706
PCT Pub. Date: Feb. 18, 2016

(65) Prior Publication Data
US 2017/0238364 A1    Aug. 17, 2017

Related U.S. Application Data

(60) Provisional application No. 62/038,073, filed on Aug. 15, 2014.

(51) Int. Cl.
*H05B 1/02* (2006.01)
*A61L 9/03* (2006.01)
*H05B 3/26* (2006.01)

(52) U.S. Cl.
CPC .............. *H05B 1/0252* (2013.01); *A61L 9/03* (2013.01); *H05B 3/262* (2013.01); *H05B 3/265* (2013.01);
(Continued)

(58) Field of Classification Search
CPC .......... A61L 9/03; H05B 3/26; H05B 1/0252; H05B 2203/021
See application file for complete search history.

(56) References Cited

U.S. PATENT DOCUMENTS 1,547,160 A    5/1923 Bailey
2,465,762 A    7/1945 Supplee
(Continued)

FOREIGN PATENT DOCUMENTS

CN    1646177 A    7/2005
CN    102247614 A    11/2011
(Continued)

OTHER PUBLICATIONS

International Search Report cited in PCT/US2015/045045, dated Nov. 10, 2015.
(Continued)

*Primary Examiner* — Dana Ross
*Assistant Examiner* — Lawrence H Samuels
(74) *Attorney, Agent, or Firm* — Quarles & Brady LLP

(57) ABSTRACT

According to one aspect, a wax warmer includes a body to support a reservoir adapted to receive a wax melt. The wax warmer also includes a heater having a first heating state to heat the wax melt from a first temperature below a melting point of the wax melt to a second temperature above the melting point of the wax melt in a predetermined amount of time. The heater has a second heating state to substantially maintain the wax melt within a temperature range above the melting point of the wax melt.

19 Claims, 30 Drawing Sheets

(52) U.S. Cl.
CPC ....... *H05B 3/267* (2013.01); *H05B 2203/021* (2013.01); *H05B 2203/022* (2013.01); *H05B 2203/037* (2013.01)

(56) References Cited

U.S. PATENT DOCUMENTS

| | | | |
|---|---|---|---|
| 2,668,993 A | 8/1950 | Bair | |
| 2,685,020 A | 7/1954 | Laibow | |
| 3,890,085 A | 6/1975 | Andeweg | |
| 4,214,146 A | 7/1980 | Schimanski | |
| 4,287,408 A | 9/1981 | Wilson | |
| 4,696,303 A | 9/1987 | Bernardini | |
| 4,731,522 A | 3/1988 | Manchester | |
| 4,781,895 A | 11/1988 | Spector | |
| 4,937,431 A * | 6/1990 | Jameson | A01M 31/008 239/59 |
| 5,171,973 A | 12/1992 | Higgins | |
| 5,175,791 A | 12/1992 | Muderlak et al. | |
| 5,578,089 A | 11/1996 | Elsamaloty | |
| 5,945,094 A | 8/1999 | Martin et al. | |
| 5,959,129 A | 9/1999 | van Dam et al. | |
| 6,019,804 A | 2/2000 | Requejo et al. | |
| 6,063,144 A | 5/2000 | Calzada et al. | |
| 6,106,597 A | 8/2000 | Starks et al. | |
| 6,214,918 B1 | 4/2001 | Johnson et al. | |
| 6,224,641 B1 | 5/2001 | Matzat et al. | |
| 6,284,007 B1 | 9/2001 | Tao | |
| 6,380,462 B1 | 4/2002 | Krindl | |
| 6,412,670 B1 | 7/2002 | Randmae et al. | |
| 6,413,476 B1 | 7/2002 | Barnhart | |
| 6,497,735 B2 | 12/2002 | Tao | |
| 6,503,285 B1 | 1/2003 | Murphy | |
| 6,599,334 B1 | 7/2003 | Anderson | |
| 6,627,857 B1 * | 9/2003 | Tanner | A61L 9/03 219/445.1 |
| 6,645,261 B2 | 11/2003 | Murphy et al. | |
| 6,663,384 B2 | 12/2003 | Papai | |
| 6,730,137 B2 | 5/2004 | Pesu et al. | |
| 6,756,567 B1 * | 6/2004 | Suen | F27B 17/00 219/424 |
| 6,758,869 B2 | 7/2004 | Roeske | |
| 6,770,104 B2 | 8/2004 | Murphy | |
| 6,773,469 B2 | 8/2004 | Murphy | |
| 6,776,808 B2 | 8/2004 | Foster | |
| 6,797,020 B2 | 9/2004 | Murphy | |
| 6,824,572 B2 | 11/2004 | Murphy | |
| 6,852,140 B1 | 2/2005 | Roeske | |
| 7,018,432 B2 | 3/2006 | Moussouni | |
| 7,046,919 B2 | 5/2006 | Shimizu et al. | |
| 7,093,949 B2 | 8/2006 | Hart et al. | |
| 7,128,766 B2 | 10/2006 | Murphy et al. | |
| 7,133,605 B2 | 11/2006 | Niemeyer | |
| 7,137,570 B2 | 11/2006 | Wheatley et al. | |
| 7,138,130 B2 | 11/2006 | Davis et al. | |
| 7,160,337 B2 | 1/2007 | Williams et al. | |
| 7,192,457 B2 | 3/2007 | Murphy et al. | |
| 7,217,301 B2 | 5/2007 | Murphy et al. | |
| 7,220,288 B2 | 5/2007 | D'Amico et al. | |
| 7,252,805 B2 | 8/2007 | Hart et al. | |
| 7,329,839 B2 | 2/2008 | Palmer | |
| 7,335,157 B2 | 2/2008 | Czupich et al. | |
| 7,387,649 B2 | 6/2008 | Tao | |
| 7,420,008 B2 | 9/2008 | Bloom | |
| 7,462,205 B2 | 12/2008 | Murphy | |
| 7,510,584 B2 | 3/2009 | Cap | |
| 7,569,084 B2 | 8/2009 | Tao et al. | |
| 7,588,607 B1 | 9/2009 | Cap | |
| 7,687,038 B2 | 3/2010 | Wheatley et al. | |
| 7,713,314 B2 | 5/2010 | Jones | |
| D618,329 S | 6/2010 | Koenig et al. | |
| 7,731,767 B2 | 6/2010 | Tao | |
| D621,923 S | 8/2010 | Koenig et al. | |
| 7,781,702 B2 | 8/2010 | Nam | |
| D629,051 S | 12/2010 | Nishimoto | |
| 7,959,689 B2 | 6/2011 | Cagle | |
| 8,021,443 B2 | 9/2011 | Murphy et al. | |
| 8,070,833 B2 | 12/2011 | Murphy | |
| 8,070,834 B2 | 12/2011 | Tao et al. | |
| 8,084,718 B1 * | 12/2011 | Shotey | A61F 7/0085 219/386 |
| 8,192,041 B2 | 6/2012 | Hsiao | |
| 8,364,028 B1 | 1/2013 | Vaske et al. | |
| 8,371,740 B2 | 2/2013 | Pestl et al. | |
| 8,496,881 B2 | 7/2013 | Pohl et al. | |
| D694,382 S | 11/2013 | Brandenburg et al. | |
| 8,716,632 B1 * | 5/2014 | Pesu | H05B 1/0269 219/433 |
| 8,772,675 B2 * | 7/2014 | Juarez | H05B 3/26 219/209 |
| 9,125,956 B2 * | 9/2015 | Juarez | H05B 3/26 |
| 2001/0001282 A1 | 5/2001 | Parmentier et al. | |
| 2003/0007887 A1 | 1/2003 | Roumpos et al. | |
| 2005/0015088 A1 | 1/2005 | Ringeisen | |
| 2005/0016985 A1 | 1/2005 | Haas et al. | |
| 2005/0150886 A1 * | 7/2005 | Niemeyer | A61L 9/03 219/385 |
| 2005/0169666 A1 | 8/2005 | Porchia et al. | |
| 2005/0184045 A1 * | 8/2005 | Shimizu | A61L 9/03 219/474 |
| 2006/0021969 A1 | 10/2006 | Wu | |
| 2006/0219694 A1 * | 10/2006 | Wu | A61L 9/03 219/400 |
| 2006/0263073 A1 * | 11/2006 | Clarke | F24H 9/2071 392/347 |
| 2006/0272199 A1 | 12/2006 | Licciardello et al. | |
| 2007/0031298 A1 | 2/2007 | Roumpos et al. | |
| 2007/0047931 A1 | 3/2007 | Niemeyer | |
| 2007/0282000 A1 | 12/2007 | Murphy et al. | |
| 2008/0038156 A1 * | 2/2008 | Jaramillo | A01M 1/2072 422/124 |
| 2008/0130266 A1 | 6/2008 | DeWitt et al. | |
| 2008/0138753 A1 | 6/2008 | Tao et al. | |
| 2008/0282601 A1 | 11/2008 | Luttke | |
| 2009/0217568 A1 | 9/2009 | Murphy et al. | |
| 2010/0024281 A1 | 2/2010 | Lemke et al. | |
| 2010/0044924 A1 | 2/2010 | Cap | |
| 2010/0096376 A1 | 4/2010 | Hsiao | |
| 2010/0205851 A1 | 8/2010 | Uptain et al. | |
| 2010/0264232 A1 | 10/2010 | Gruenbacher et al. | |
| 2010/0270943 A1 * | 10/2010 | Cook | A61L 9/03 315/291 |
| 2010/0308126 A1 | 12/2010 | Gruenbacher et al. | |
| 2011/0110072 A1 | 5/2011 | Hsiao | |
| 2011/0110824 A1 | 5/2011 | Hsiao | |
| 2012/0024837 A1 * | 2/2012 | Thompson | A61L 9/03 219/433 |
| 2012/0070132 A1 | 3/2012 | Napier | |
| 2012/0183280 A1 | 7/2012 | Kowalec et al. | |
| 2012/0318779 A1 | 12/2012 | Juarez | |
| 2012/0318780 A1 * | 12/2012 | Juarez | H05B 3/26 219/209 |
| 2013/0020307 A1 | 1/2013 | Ashton et al. | |
| 2013/0170184 A1 | 7/2013 | Browder et al. | |
| 2013/0327842 A1 | 12/2013 | Seiler et al. | |
| 2014/0014641 A1 | 1/2014 | Propes | |
| 2014/0017136 A1 | 1/2014 | Wirz | |
| 2014/0119715 A1 * | 5/2014 | Tix | H05B 1/023 392/466 |
| 2015/0174278 A1 | 6/2015 | Belongia | |
| 2015/0283280 A1 | 10/2015 | Belongia | |
| 2015/0305089 A1 | 10/2015 | Belongia et al. | |
| 2016/0375168 A1 * | 12/2016 | Hsiao | A61L 9/03 392/390 |
| 2017/0232126 A1 * | 8/2017 | Faterioun | A61L 9/03 239/136 |

FOREIGN PATENT DOCUMENTS

| | | |
|---|---|---|
| CN | 202802263 U | 3/2013 |
| CN | 202909152 U | 5/2013 |
| CN | 103460792 A | 12/2013 |
| CN | 203708514 U | 7/2014 |
| WO | 2002/100449 A1 | 12/2002 |

(56) References Cited

FOREIGN PATENT DOCUMENTS

| WO | 2005070156 A2 | 8/2005 |
| WO | 2007/075645 A1 | 7/2007 |
| WO | 2010088175 A1 | 8/2010 |

OTHER PUBLICATIONS

Examination Report received in Australian Patent Application No. 2015301635, dated Jun. 20, 2015, 3 pages.
PCT/US2015/023764 International Search Report and Written Opinion dated Jan. 16, 2015.
Examination Report No. 1 for standard patent application received in Australian Patent Application No. 2015301635, dated Feb. 24, 2017, 3 pages.
Examination Report No. 2 for standard patent application received in Australian Patent Application No. 2015301635, dated Jun. 20, 2017, 3 pages.
Examination Report No. 3 for standard patent application received in Australian Patent Application No. 2015301635, dated Aug. 30, 2017, 5 pages.
First Office Action and search report issued in corresponding Chinese Application No. 201580056031.1, dated Apr. 19, 2019, 18 pages.

* cited by examiner

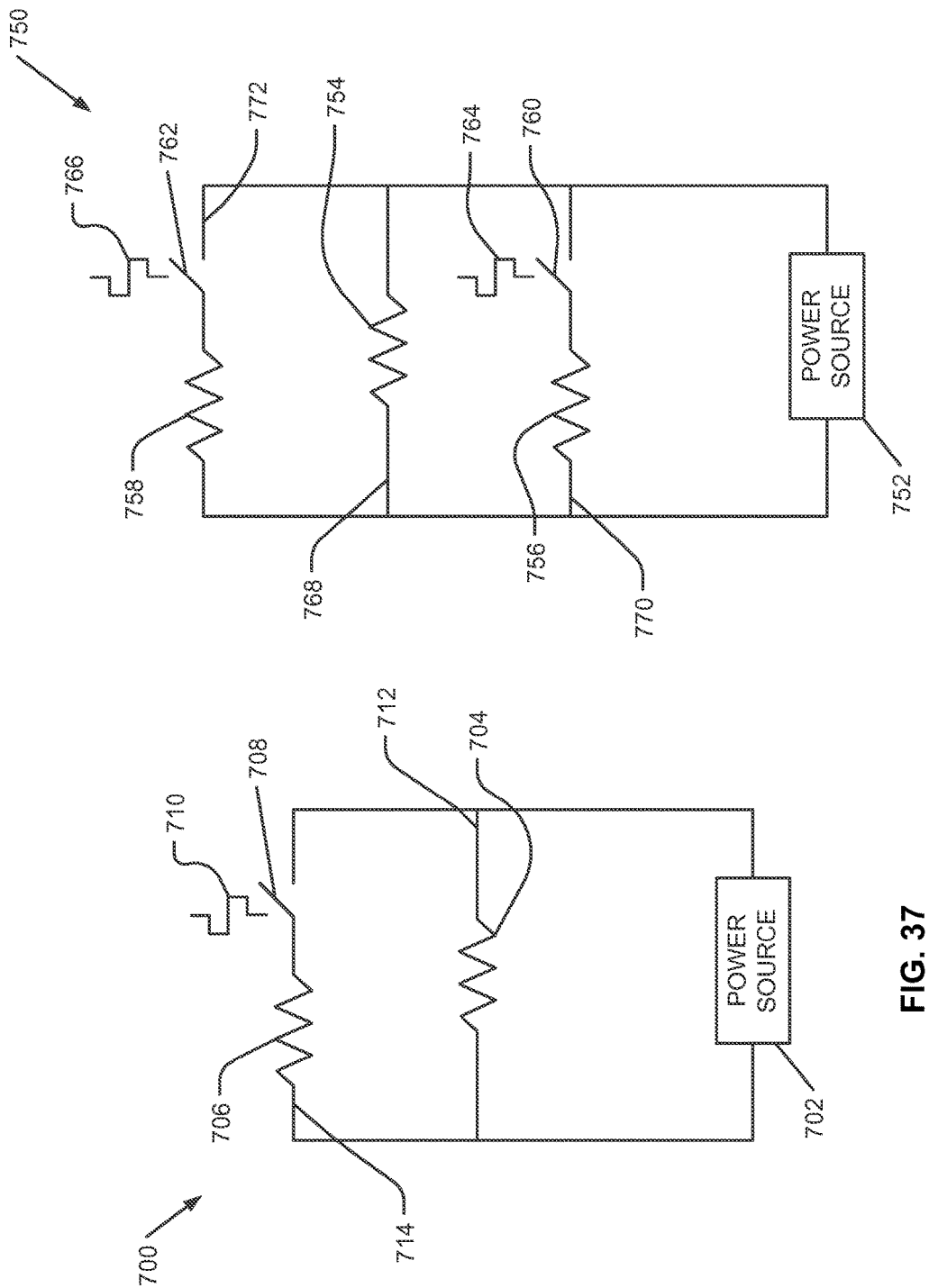

WAX WARMERS

CROSS REFERENCE TO RELATED APPLICATIONS

This application claims the benefit of U.S. Provisional Application No. 62/038,073, which was filed on Aug. 15, 2014 and entitled "Wax Warmers." U.S. Provisional Application No. 62/038,073 is incorporated by reference herein in its entirety.

REFERENCE REGARDING FEDERALLY SPONSORED RESEARCH OR DEVELOPMENT

Not applicable

SEQUENTIAL LISTING

Not applicable

BACKGROUND

Field of the Disclosure

The present disclosure generally relates to a wax warmer, and more specifically, to a wax warmer for use with a wax melt to dispense materials into the surrounding environment.

Description of the Background of the Disclosure

Candles have been used for centuries to provide illumination and pleasant aromas to the surrounding environment. At its most basic level, a candle consists of a wick dipped in wax. The wick is lit and provides light while the burning or melting wax may provide a pleasant aroma. Alternatively, unscented or scented candles or wax melts can be placed in a warmer. These candles or warmers may also be used to provide more than just illumination and/or pleasant fragrances. For instance, candles and warmers may be placed outside around a patio or deck. The wax or oil may include materials with insect repellant properties along with providing a pleasant aroma and/or illumination. Generally, users can burn or warm waxes and oils to provide desired effects to the surrounding atmosphere or environment.

Traditional warmers and candles may have some drawbacks. Candles may be forgotten and left unsupervised and may represent a fire hazard. Also, a candle flame may be extinguished with a slight breeze or gust of wind. Further, melted wax may splatter or make a mess with traditional candles. An additional drawback associated with candles is the inability to control the intensity of the heat being provided to the scented material. A candle flame is not easily adjustable and thus the amount of heat the flame provides to the infused wax or oil does not allow a user to vary the strength of the fragrance introduced into the surrounding environment.

Traditional electric wax warmers have a heater in thermal contact with a reservoir for holding a wax melt or infused oil. The heater replaces the candle in a traditional warmer and melts the wax or heats the oil in the reservoir resulting in the same benefits as previously mentioned. The lack of a flame reduces the risk associated with traditional warmers and candles. However, an amount of time employed by traditional electric wax warmers to melt the wax melt and/or heat the oil may be undesirably long, thereby delaying an introduction of the fragrant and/or other materials into the surrounding environment.

SUMMARY

According to one aspect, a wax warmer includes a body to support a reservoir adapted to receive a wax melt. The wax warmer also includes a heater including a first resistor and a second resistor. The heater is to flow electrical current through the first resistor and the second resistor during a first heating state to heat the wax melt from a first temperature below a melting point of the wax melt to a second temperature above the melting point of the wax melt. The heater is to flow electrical current through the first resistor and prevent electrical current from flowing through the second resistor during a second heating state to substantially maintain the temperature of the wax melt at the second temperature.

According to another aspect, a wax warmer includes a body to support a reservoir adapted to receive a wax melt. The wax warmer also includes an electrical circuit operatively coupled to the body to heat the wax melt from a first temperature below a melting point of the wax melt to a second temperature above the melting point of the wax melt. The electrical circuit has a first heating state and a second heating state. The electrical circuit in the first heating state has a first overall resistance, and the electrical circuit in the second heating state has a second overall resistance greater than the first electrical resistance.

According to another aspect, a wax warmer includes a body to support a reservoir adapted to receive a wax melt. The wax warmer also includes a heater having a first heating state to heat the wax melt from a first temperature below a melting point of the wax melt to a second temperature above the melting point of the wax melt in a predetermined amount of time. The heater has a second heating state to substantially maintain the wax melt within a temperature range above the melting point of the wax melt.

BRIEF DESCRIPTION OF THE DRAWINGS

FIG. 37 is a schematic depiction of a heating control circuit disclosed herein, which may be used to implement the wax warmers of FIGS. 1-36;

FIG. 38 is a schematic depiction of another heating control circuit disclosed herein, which may be used to implement the wax warmers of FIGS. 1-36;

Other aspects and advantages of the examples disclosed herein will become apparent upon consideration of the following detailed description, wherein similar structures have similar reference numerals.

DETAILED DESCRIPTION

Figure 1:
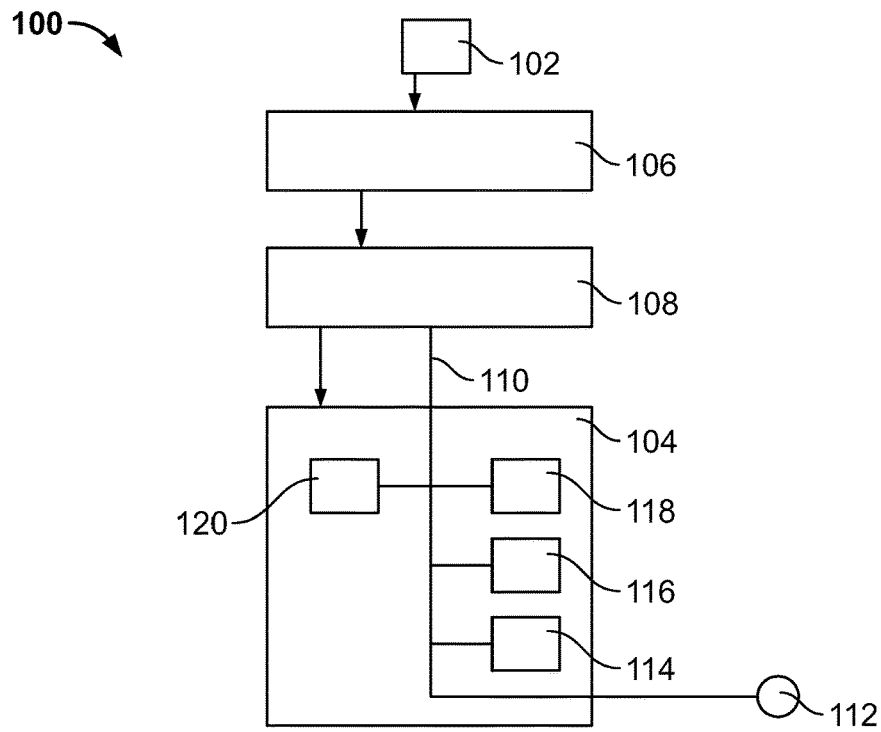
FIG. 1 is a schematic depiction of a wax warmer with a wax melt.

Referring to FIG. 1, a schematic representation of a wax warmer 100 is depicted. The wax warmer 100 is designed to heat a wax melt 102 and thereby release a fragrance or other volatile material contained therein into the surrounding environment. The wax warmer 100 generally includes a base or body 104, a reservoir 106, and a heater assembly 108. The wax warmer 100 is constructed such that the base 104 supports the heater assembly 108 and the heater assembly 108 supports the reservoir 106 during normal operation (see arrows in FIG. 1). The heater assembly 108 includes an electrical cord 110 for providing electrical power to the heater assembly 108. The electrical cord 110 may pass through the base 104 to connect to an electrical outlet 112. In some embodiments, the cord 110 may connect to the heater assembly 108 with a plug (not shown) adapted to mate with a socket (not shown) on the heater assembly 108. In other embodiments the cord 110 may be permanently attached to the heater assembly 108. Another alternative embodiment may include batteries (not shown) to provide electrical power to the heater assembly 108.

Figure 2:
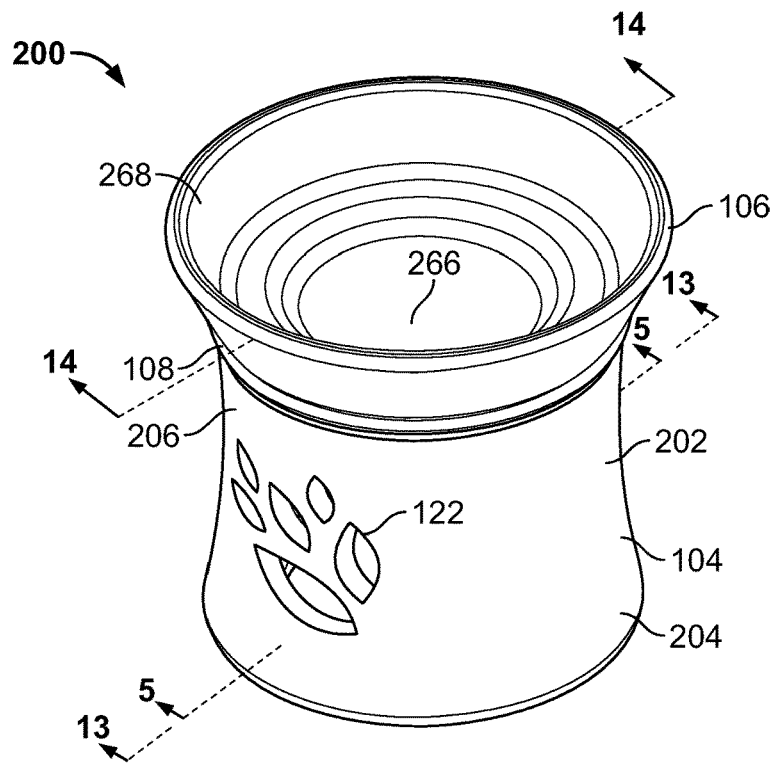
FIG. 2 is a top and front isometric view of a wax warmer.
Figure 3:
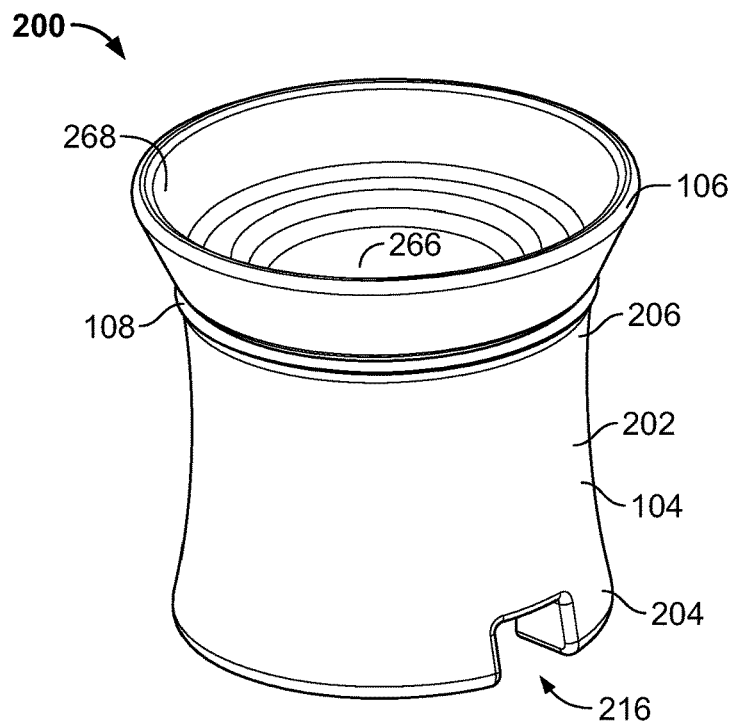
FIG. 3 is a top and rear isometric view of the wax warmer of FIG. 2.

It is contemplated that the cord 110 may include a switch 114 and/or a control module 116 in some embodiments. The control module 116 and the switch 114 may be inline components of the cord 110 such that they are external to the base 104 and accessible by a user when the wax warmer 100 is configured for normal operation. Alternatively, the base 104 may include support structure (not shown) for the switch 114 and the control module 116 to be retained within the base 104 and accessed by the user through apertures (not shown) in the base 104 or otherwise mounted to a sidewall thereof. It is also contemplated that the wax warmer 100 may include sensors 118. The control module 116 may receive signals for the sensors 118 and include the capability to be programmed by the user for different modes of operation. The sensors 118 may be mounted on the cord 110 or they may be mounted on the base 104. The cord 110 may also include one or more light emitting diodes (LEDs) 120 as an inline component. The LEDs 120 may provide indication to the user that the wax warmer 100 is operational, is inoperational, is in a standby mode, is in a lockout mode, is detecting sensory input, has detected sensory input, etc. Alternatively, the LEDs 120 may provide illumination for aesthetic purposes or some other functional purpose as would be known to one of ordinary skill. In some embodiments, the LEDs 120 may be viewed through apertures 122 (See FIG. 2) in the base 104. The LEDs 120 may be part of the control module 116 and/or the switch 114.

Figure 1A:
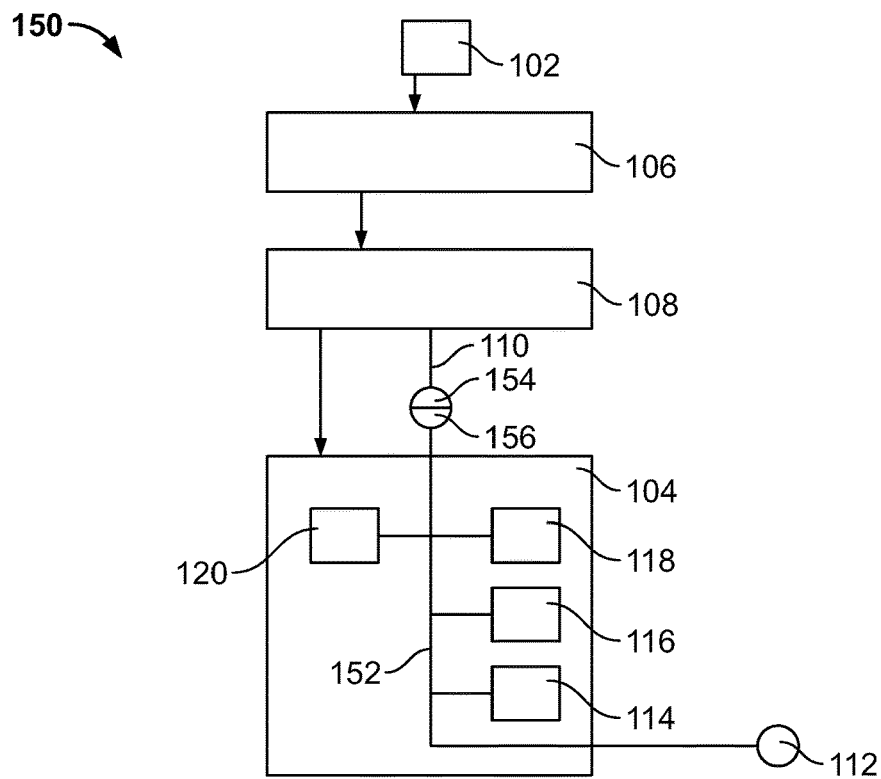
FIG. 1A is schematic depiction of another embodiment of a wax warmer with a wax melt.

Now turning to FIG. 1A, another schematic embodiment of a wax warmer 150 is depicted. The wax warmer 150 may include a wiring harness 152 or other internal electrical structure mounted in the body 104 that may include one or more of the LEDs 120, the control module 116, and the switch 114 as described above. The cord 110 may include a plug 154 that mates with a socket 156 of the wiring harness. The wiring harness 152 thereby provides electrical power to the heater module 108 and other electrical components through a connection to the external electrical outlet 112.

Referring to FIGS. 1 and 1A, the wax warmers 100, 150 are contemplated to be modular in nature. The reservoir 106, the heater assembly 108, and the base 104 are therefore reconfigurable or replaceable during the normal operation of the wax warmers 100, 150. Normal operation of the wax warmers 100, 150 comprises the time and actions taken by a user in assembling and/or configuring the wax warmer 100, 150 through manipulation of the components 104, 106, 108 to utilize the wax warmer 100, 150 to warm the wax melt 102. Normal operation would also include the time and actions taken by the user in reconfiguring the wax warmer 100, 150 by replacing one or more of the components 104, 106, 108 with a replacement component 104, 106, 108. Normal operation does not include a manufacturing step upstream of a use by an end user of the wax warmer 100, 150. Normal use also constitutes a point in time when tools, besides manual manipulation by the user, are no longer required to assemble or configure the wax warmer 100, 150 and/or any replacement component 104, 106, 108. The user may purchase the reservoir 106, the heater assembly 108, and the base 104 together as a starter kit or, alternatively, may purchase or otherwise procure one or more of the reservoir 106, heater assembly 108 or base 104 separately. For a user to enjoy the modular nature of the wax warmer 100, no special skills should be required to configure and reconfigure the unit for normal operation. The process (to be described in detail later) of retaining the reservoir 106, the heater assembly 108, and the base 104 in a normal operational configuration is preferably easy for a layperson to accomplish.

Referring to FIGS. 2-5, another embodiment of a wax warmer 200 is depicted, which may encompass any of the structure or operational characteristics of the wax warmers 100, 150. Common elements shared between the embodiments in the present application will share the same numbers. The wax warmer 200 includes a base 104, a reservoir 106, and a heater assembly 108. The base 104 is fashioned to house the heater assembly 108 and provide a support structure for the reservoir 106. The wax warmer 200 is generally described to include the aforementioned components, but the wax warmer 200 may be adapted to add or remove various components according to specific user requirements.

Figure 4:
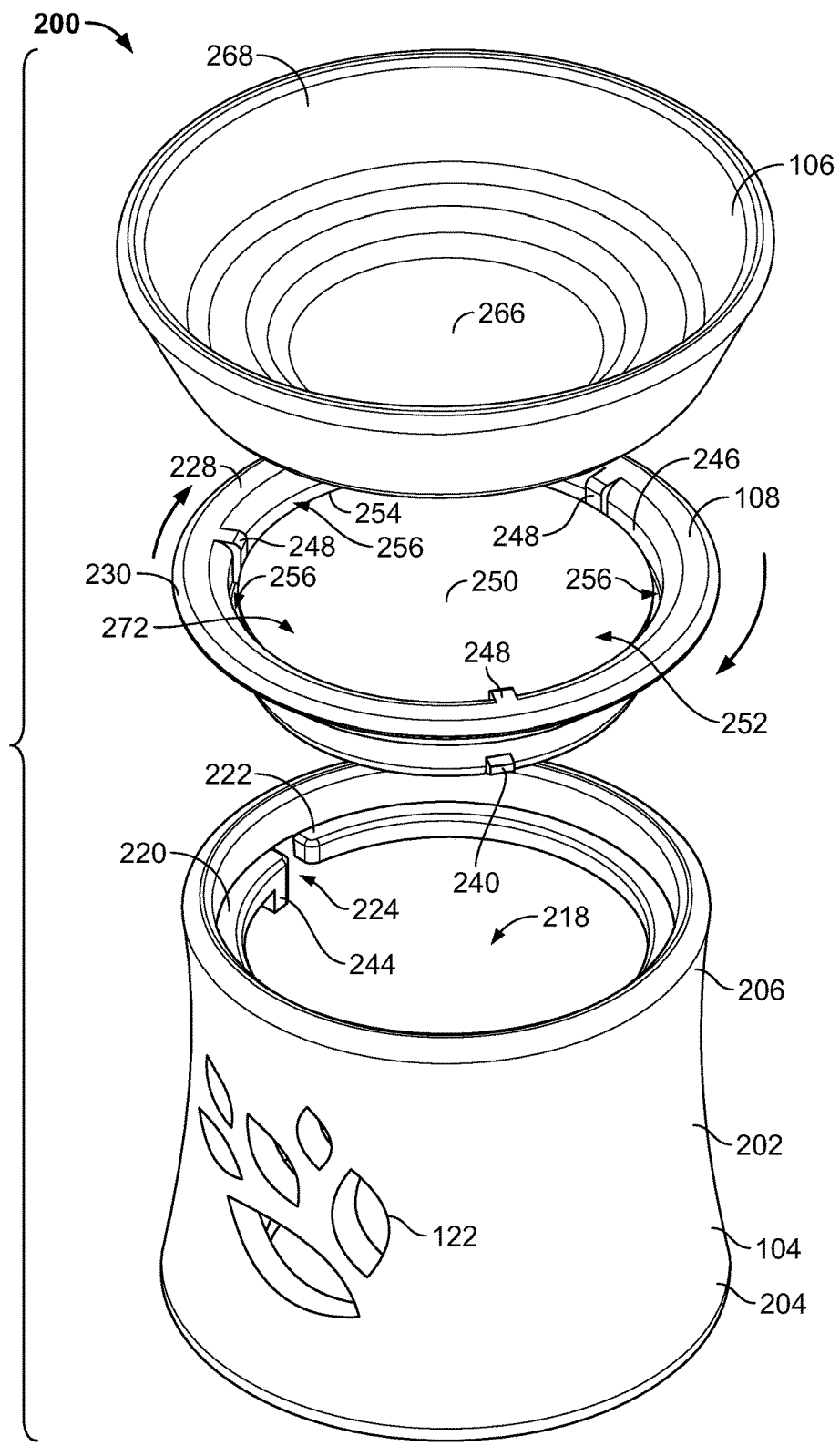
FIG. 4 is an exploded isometric view of the wax warmer of FIG. 2.
Figure 5:
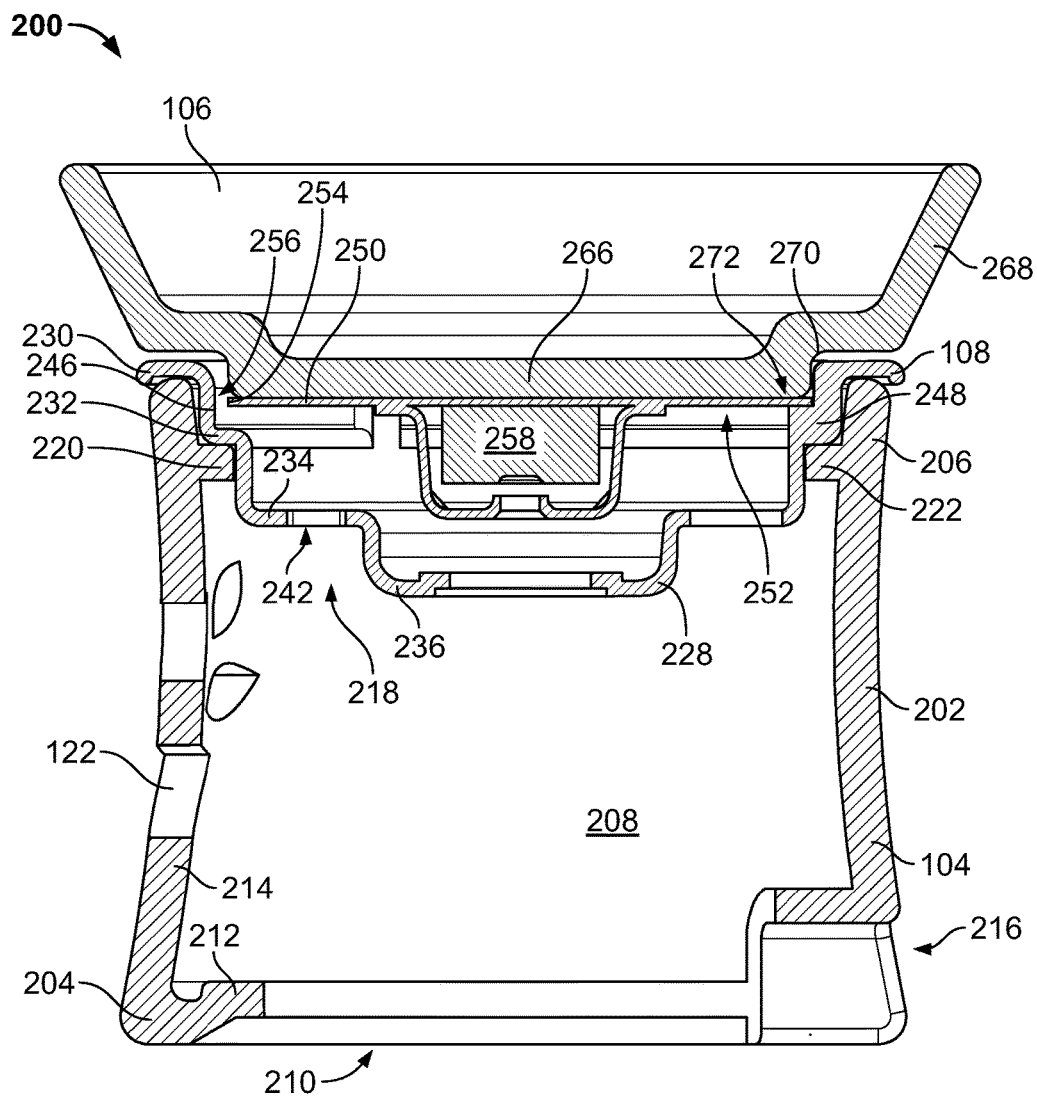
FIG. 5 is a cross-sectional view of the wax warmer of FIG. 2 taken generally along the line 5-5 of FIG. 2.

With respect to FIGS. 4 and 5, the base 104 includes a sidewall 202 having a bottom end 204 and a top end 206. In the present embodiment, the sidewall 202 is generally cylindrical in shape and defines an inner space 208 (see FIG. 5). The bottom end 204 defines a first opening 210. A lip 212 extends from an inner surface 214 of the sidewall 202 adjacent the bottom end 204. The bottom end 204 or the lip 212 may include extensions (not shown) or other structures (e.g., feet, pads, elements with high coefficients of friction, etc.) generally known to those having ordinary skill in the art to provide stability to the wax warmer 200. A cord aperture 216 (see FIGS. 3 and 5) is also provided proximal to the bottom end 204 of the sidewall 202. Preferably, the cord aperture 216 provides a pass-through for an electrical cord (not shown) in electrical communication with the heater assembly 108 and other electrical components.

Figure 6:
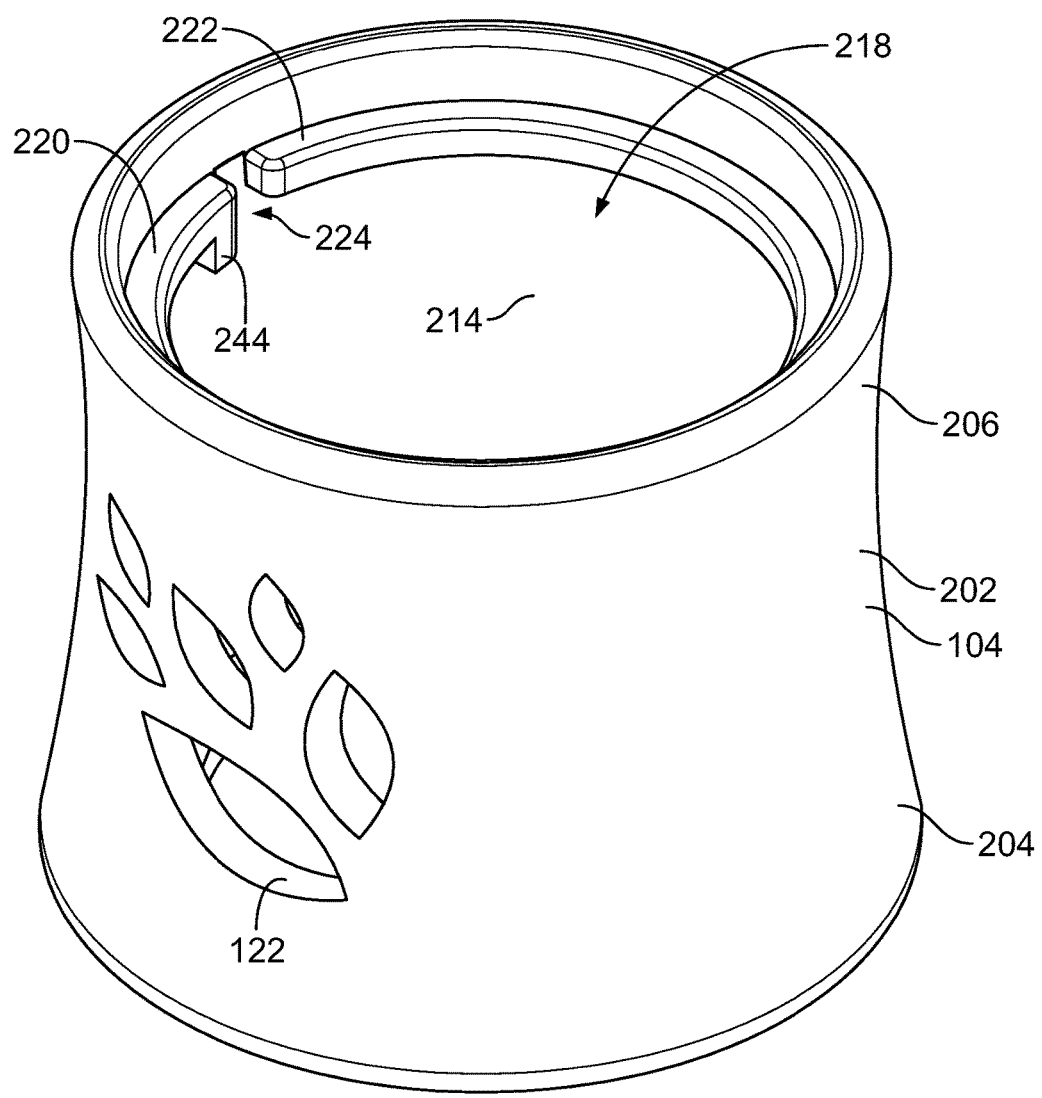
FIG. 6 is a top, front, and right side isometric view of a base of the wax warmer of FIG. 2.
Figure 7:
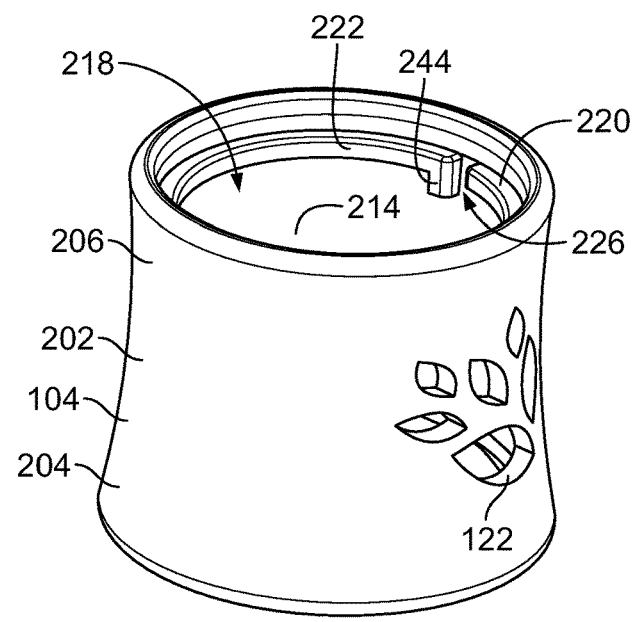
FIG. 7 is a top, front, and left side isometric view of a base of the wax warmer of FIG. 2.
Figure 8:
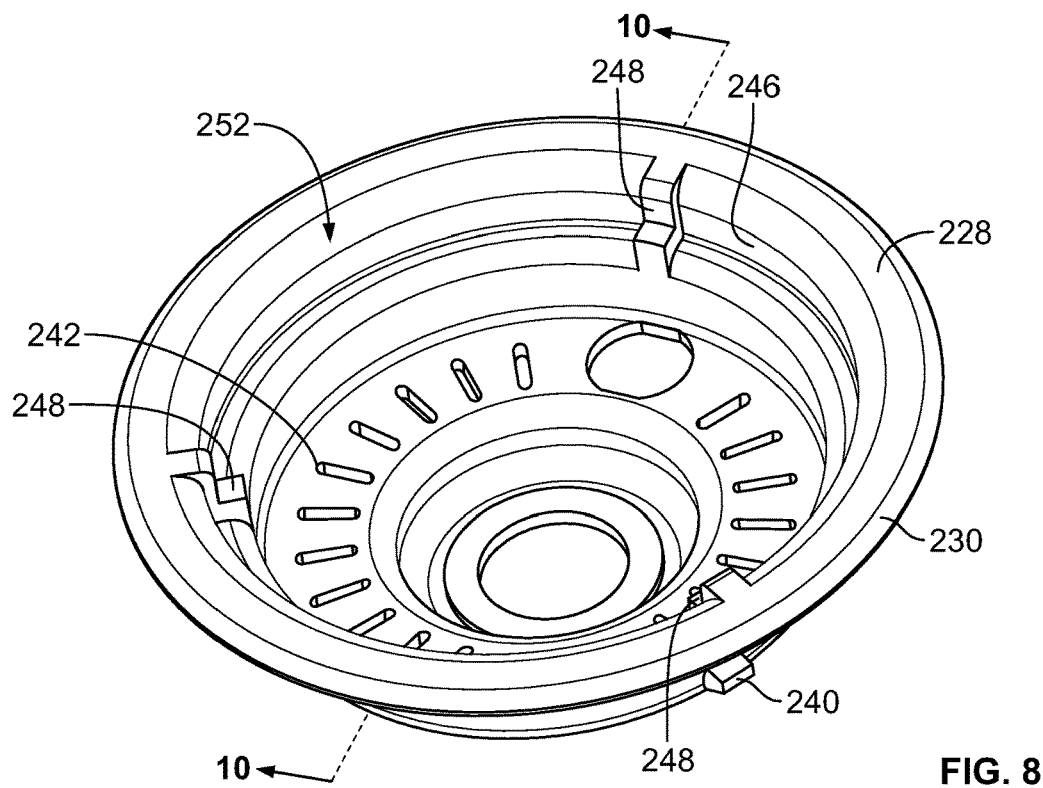
FIG. 8 is a top and front isometric view of a heater assembly housing of the wax warmer of FIG. 2.
Figure 9:
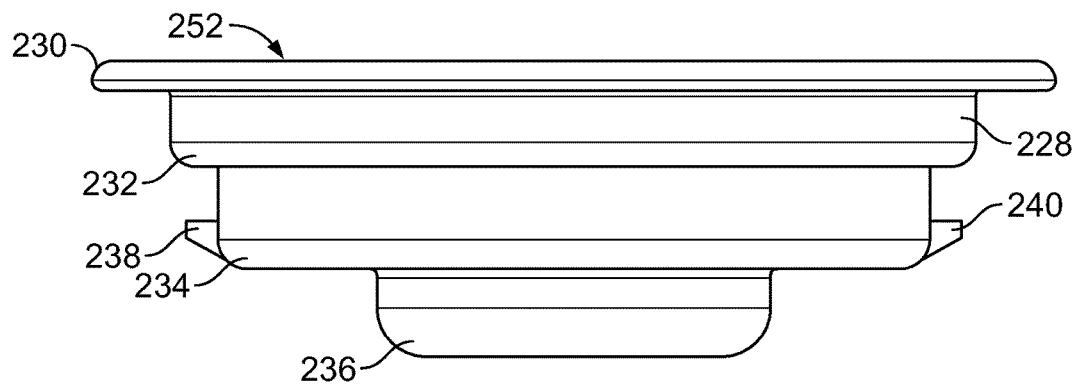
FIG. 9 is a side elevational view of the heater assembly housing of FIG. 8.
Figure 10:
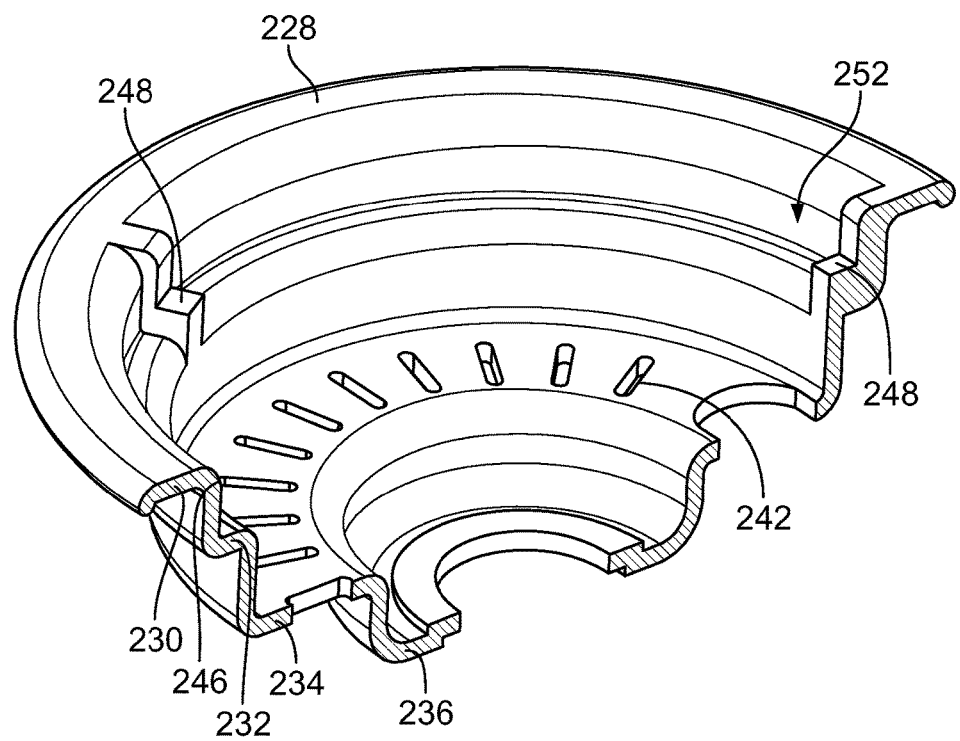
FIG. 10 is a cross-sectional view of the heater assembly housing of FIG. 8 taken generally along the line 10-10 of FIG. 8.
Figure 11:
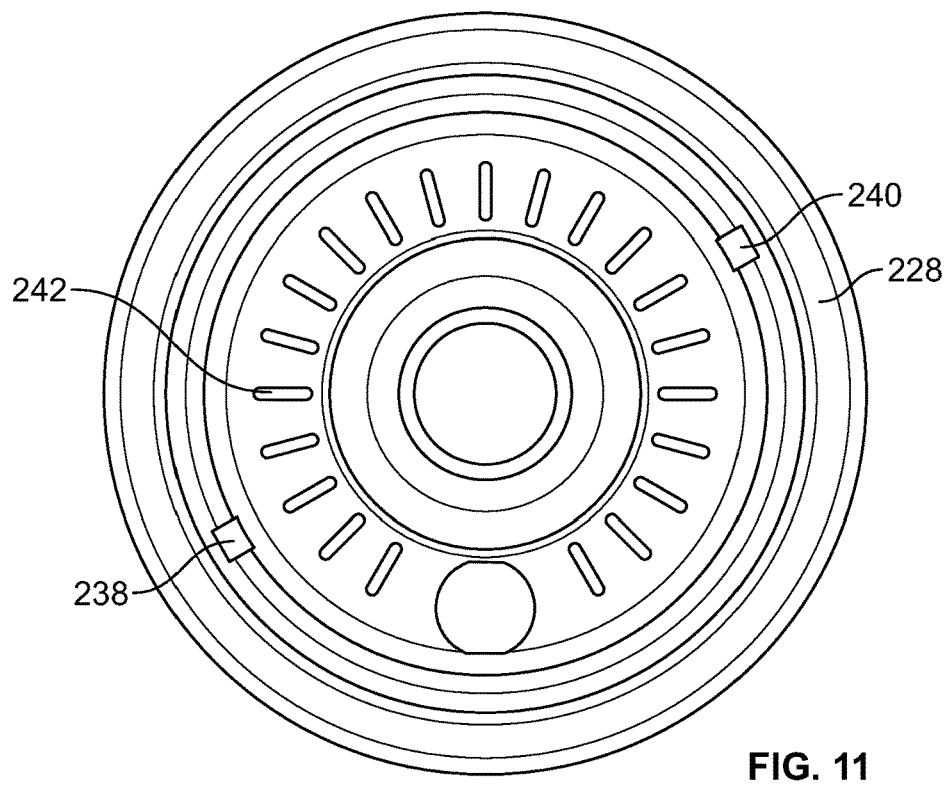
FIG. 11 is a bottom elevational view of the heater assembly housing of FIG. 8.

Turning again to FIGS. 4-7, a second opening 218 is provided at the top end 206 of the sidewall 202. A first flange 220 and a second flange 222 extend from the inner surface 214 of the sidewall 202 proximal to the top end 206. A first gap 224 and a second gap 226 are defined by the first flange 220 and the second flange 222 (see FIGS. 6 and 7). The second opening 218 and the first and second flanges 220, 222 and the first and second gaps 224, 226 are adapted to receive the heater assembly 108.

With reference to FIGS. 8-11, the heater assembly 108 includes a housing 228. The housing 228 forms a cup-like structure with three annular sections extending downward from a U-shaped lip 230. The housing 228 includes a first section 232, a second section 234, and a third section 236. A first lug 238 and a second lug 240 extend radially outward from the second section 234. The second section also includes inlet vents 242. In the present embodiment, the inlet vents 242 are oval shaped apertures.

The heater assembly 108 is adapted to be retained within the top end 206 of the sidewall 202 of the base 104. Specifically, the U-shaped lip 230 and the first section 232 are adapted to be retained by the top end 206 of the sidewall 202 and the flanges 220, 222, respectively. During placement of the heater assembly 108 into the first opening 218, the first and second lugs 238, 240 are sized to pass through the first and second gaps 224, 226. The user must align the lugs 238, 240 with the gaps 224, 226 to insert the heater assembly 108 into the base 104. After insertion, the lugs 238, 240 are below the level of the flanges 220, 222. The user thereafter rotates the heater assembly 108 until the lugs 238, 240 contact stops 244 (see FIGS. 6 and 7) extending downward from the flanges 220, 222. It is also contemplated that the releasable structure of the components of the wax warmer 200 described above may take other forms. For example, the arrangement between the lugs 238, 240 of the heater module 108 and the flanges 220, 222 and gaps 224, 226 may be replaced with a threaded structure (not shown).

Turning again to FIGS. 8 and 10, an inner surface 246 of the first section 232 includes three spacer projections 248. Now referring to FIG. 5, a heating plate or plate 250 is supported in an upper opening 252 defined by the inner surface 246 and the spacer projections 248. It is contemplated that the heating plate 250 may be made of metal. Alternatively, the heating plate may be made of any other materials (e.g., high temperature plastics) known to one having skill in the art that may provide adequate thermal transfer. The heating plate 250 is supported by the spacer projections 248 such that a circumferential edge 254 of the heating plate 250 is spaced apart from the inner surface 246 of the housing 228 except where contact is made with the spacer projections 248. This arrangement forms outlet vents 256 between the circumferential edge 254 of the heating plate 250 and the inner surface 246 of the housing 228. The heating plate 250 is in thermal contact with a heating element or heater 258 within the housing 228 of the heater assembly 108. The heating plate 250, the heating element 258, and the housing 228 may be secured together by known means. For clarity, the electrical and mechanical structure within the heating module and the electrical cord to provide electrical power have been excluded from the figures.

Figure 12:
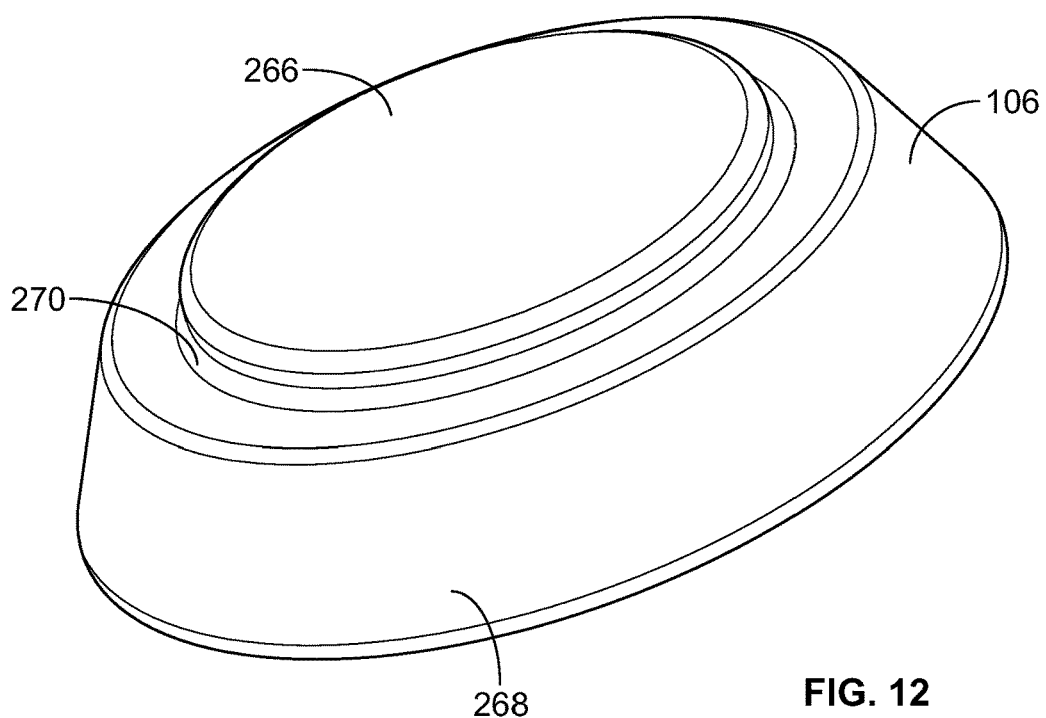
FIG. 12 is a bottom isometric view of a reservoir of the wax warmer of FIG. 2.

Turning to FIGS. 4, 5, and 12, the reservoir 106 includes a lower cylindrical projection comprising a bottom wall 266. The bottom wall 266 and a sidewall 268 form a cup-like structure for containing the wax melt 102 in a pre-operative solid state and in an operative state when the wax melt 102 is in a liquid or semi-liquid state. The reservoir 106 further includes an annular cut-out 270. When the heating plate 250 rests on the spacer projections 248 of the heater assembly housing 228, the plate 250 and the inner surface 246 of the housing 228 define a recess 272. The recess 272 is configured to receive the cylindrical projection of the bottom wall 266 of the reservoir 106. Further, the cut-out 270 of the reservoir 106 is adapted to receive an interior portion of the U-shaped lip 230 of the heater module housing 228. The interaction of the U-shaped lip 230 with surfaces defining the cut-out 270 and the cylindrical projection of the bottom wall 266 with surfaces defining the recess 272 retain the reservoir 106 on the heater assembly 108.

The bottom wall 266 of the reservoir 106 is generally flat to provide maximum thermal contact with the heating plate 250. The present arrangement also ensures that the reservoir 106 is centered on the heater assembly 108 for improved thermal transfer from the heating element 258 to the wax melt 102. Also, the reservoir 106 may be easily replaced with another reservoir (not shown) that has the same structural characteristics but a different aesthetic design.

Figure 13:
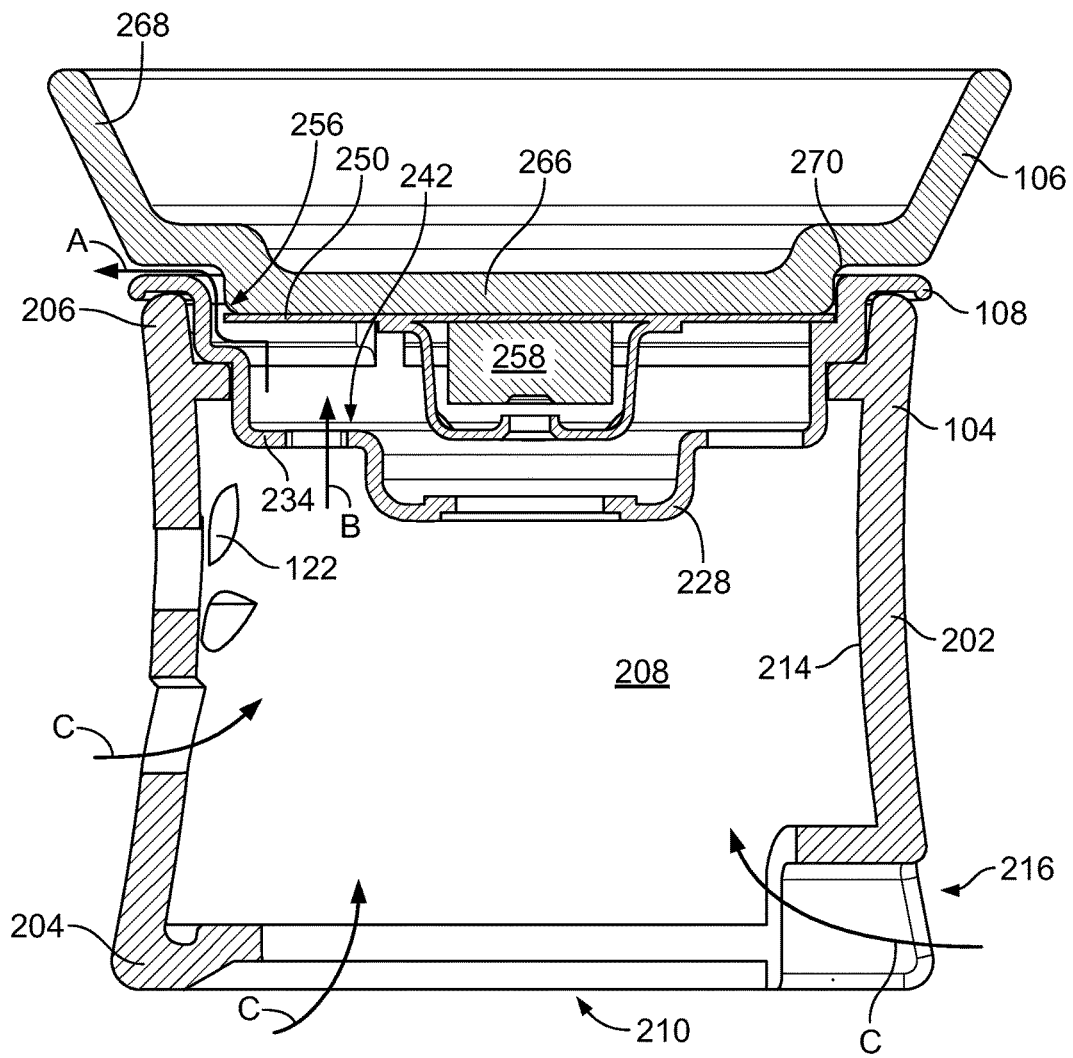
FIG. 13 is a cross-sectional view of the wax warmer of FIG. 2 taken generally along the line 13-13 of FIG. 2 depicting the air flow through the wax warmer.

Referring to FIG. 13, during operation the heating element 258 heats the wax melt 102 in the reservoir 106 through heat transferred through the heating plate 250 and the bottom wall 266. Some heat will also be transferred to the air within the heating assembly 108. The heated air will rise up through the outlet vents 256 and up the sidewall 268 of the reservoir 106 (see the arrow A). As the heated air rises out of the heater assembly 108, cooler air from the inner space 208 will be drawn up into the heater assembly 108 through the inlet vents 242 of the second section 234 of the housing 228 (see the arrow B). Air may be drawn into the inner space 208 of the base 104 through any of the apertures 122, the cord aperture 216, or the first opening 210 of the base (see the arrow C). Thus, while the heating element 258 is operational, a flow of air from outside the base 104, through the inner space 208 and the heater assembly 108, and up past the reservoir 106 into the surrounding environment will be created. This flow of air may help with the distribution of fragrance or volatile material from the wax melt 102 and may also help prevent the heating element 258 from overheating.

It has been contemplated that the base 104 and the reservoir 106 are preferably made from a ceramic material. However, any other materials as known to those having ordinary skill in the art may be used, such as plastic, metal, stone or other natural materials. The base 104, the reservoir 106, and the heater assembly 108 may take any geometric shape, e.g. a cylinder or square, to provide different appearances. Further, the exterior surfaces of the base 104 and the reservoir 106 may be provided with any type of surface indicia, raised patterns, or any other decorations to configure the wax warmer 100 for aesthetic purposes.

In some embodiments, the heating element 258 is a resistive type heater. However, the heating element 258 may be any type of heater. For example, the heater may be a positive thermal coefficient heater or an inductive type heater. In other examples, the heating element 258 may be replaced by a series of heaters or any known heating arrangement that allows the heating element 258 to make sufficient thermal contact with the heating plate 250.

The wax melt 102 is wickless and may comprise any geometric shape. In some embodiments, the wax melt 102 has a generally square shape with slightly rounded curvature imparted thereto at an area where sidewalls of the wax melt intersect with each other. There are no substantial surface interruptions beyond minor surface irregularities formed during the manufacturing process. It is contemplated that the shape of the wax melt 102 may be configured to be beneficial for manufacturing purposes or aesthetic reasons or both.

Figure 14:
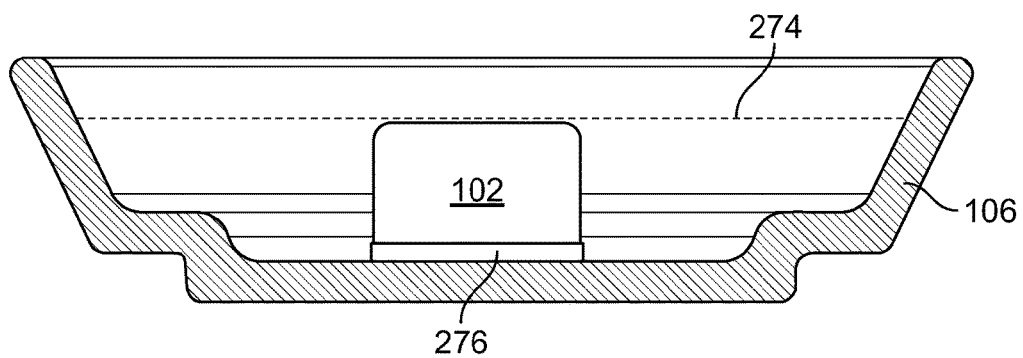
FIG. 14 is a cross-sectional view of the reservoir of the wax warmer of FIG. 2 taken generally along the line 14-14 of FIG. 2.

It is also envisioned that the wax melt 102 may be secured to the reservoir 106 prior to normal use by the user. For example, the reservoir 106 may be purchased as part of a kit or an individual item that includes the wax melt 102. It is considered that the wax melt 102 may be wrapped, e.g., in a plastic or malleable material, with the reservoir 106, or secured by way of a blister cartridge or shell that retains and secures the reservoir 106 with the wax melt 102 (see for example 274 in FIG. 14). In one embodiment, the wax melt 102 is irremovably attached to the reservoir 106 prior to purchase by the user and prior to melting of the wax melt 102 during normal use of the wax warmer 200. Several non-exhaustive securing mechanisms (see for example 276) include an adhesive, a chemical bond between the wax melt 102 and a surface of the reservoir 106, an interference fit between surfaces of the wax melt 102 and surfaces of the reservoir 106, and a projection extending from the reservoir 106 into the wax melt 102. In embodiments utilizing a wax melt 102 secured to the reservoir 106, it is further contemplated that the reservoir 106 alone may be removable and replaceable with a second reservoir 106. However, it is also anticipated that any of the components of the wax warmer 200 may be interchangeably removable as previously described.

It is also contemplated that the wax warmer 200 may be part of a kit that may include one or more wax melts 102, the base 104, the reservoir 106, the heater assembly 108, and instructions for the assembly and use thereof. The user may purchase the kit and possibly one or more replacement components. The instructions may include the steps of removing the components 104, 106, 108 and the wax melt 102 from any packaging materials; assembling the wax warmer 200 by placing the heater assembly 108 on the base 104 and the reservoir 106 on the heater assembly 108; making any required electrical connections; placing a wax melt within the reservoir 106; switching on the wax warmer 200; turning off the wax warmer 200; replacing the wax melt 102 or adding additional wax melts 102; changing from one type of wax melt 102 to another different type of wax melt 102; instructing the user on proper safety precautions; and reconfiguring and/or disassembling the wax warmer 200.

The instructions may include instructing the user to replace at least one of a first base 104, a first reservoir 106, and a first heater assembly 108 with a second base 104, a second reservoir 106, and a second heater assembly 108. The user may replace any of the components 104, 106, 108 for the purpose of customizing the wax warmer 200 or replacement of a worn or damaged component 104, 106, 108. Normal use of the wax warmer 200 may include configuring and reconfiguring the wax warmer 200.

From the description above it is contemplated that several manufacturing advantages should be apparent. First, the wax warmer 200 does not require only a single supplier to manufacture all the components. For example, a ceramic supplier may manufacture the base 104 and the reservoir 106, while a separate manufacturer may be used for the heater assembly 108. Second, complex assembly steps have been reduced or eliminated through the use of the provided components 104, 106, 108. Third, the flexibility provided to the manufacturer in designing and building the wax warmer 200 allows for much greater flexibility for the customer to customize the wax warmer.

Referring to FIGS. 15-18, another wax warmer 300 is depicted. The wax warmer 300 is designed to heat a wax melt 302 (see FIG. 16) and thereby release a fragrance or other material contained therein into the surrounding environment. The wax warmer 300 generally includes a body 304, a reservoir 306, and a heater assembly 308 (see FIGS. 17 and 18). The body 304 is fashioned to house the heater assembly 308 and provide a support structure for the reservoir 306. The wax warmer 300 is generally described to include the aforementioned components, but the wax warmer 300 may be adapted to add or remove various components according to specific user requirements.

Figure 18:
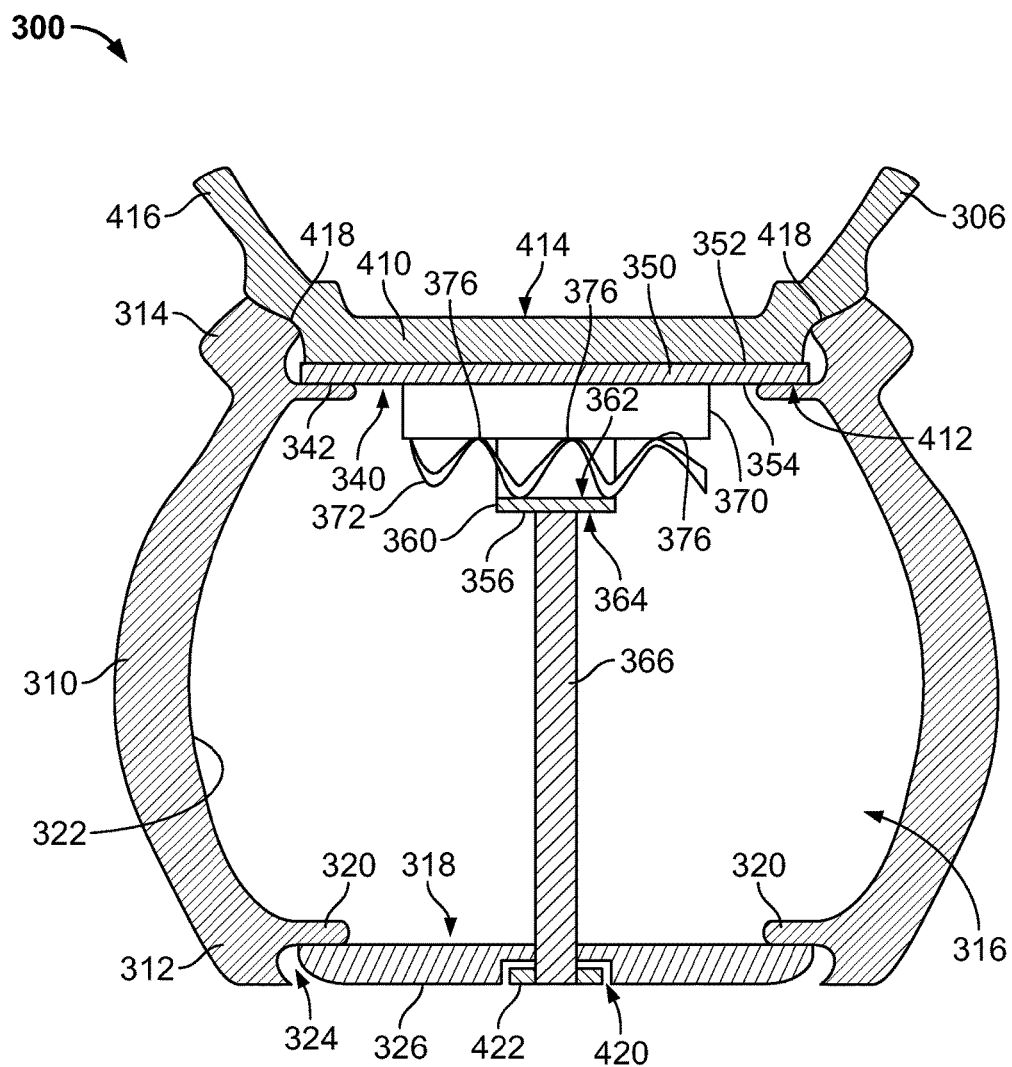
FIG. 18 is a cross-sectional view of the wax warmer taken generally along the line 18-18 of FIG. 15.
Figure 19:
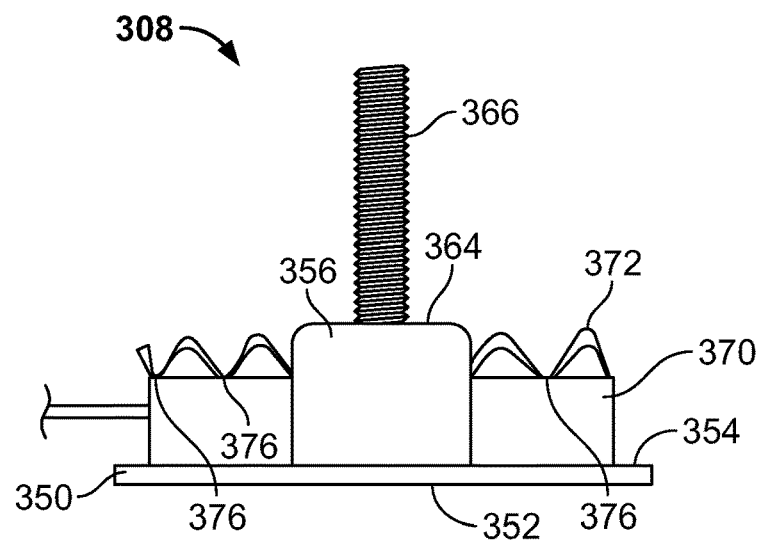
FIG. 19 is a front elevational view of another heater assembly.
Figure 20:
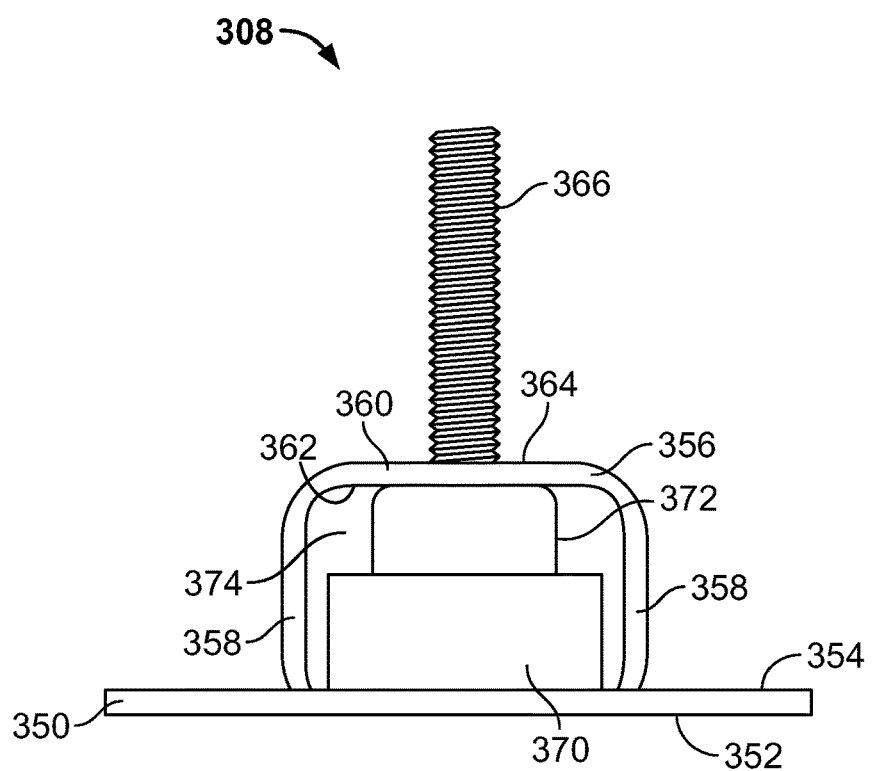
FIG. 20 is a side elevational view of the heater assembly of FIG. 19.

With respect to FIG. 18, the body 304 includes a sidewall 310 having a bottom end 312 and a top end 314. In the present embodiment, the sidewall 310 is generally cylindrical in shape and defines an inner space 316. The bottom end 312 defines a first opening 318. A lip 320 extends from an inner surface 322 of the sidewall 310. The bottom end 312 and the lip 320 form a recess 324 adapted to receive a base plate 326. The base plate 326 may include extensions (not shown) or other structures (feet, pads, structures with high coefficients of friction, etc.) generally know to those having ordinary skill in the art to provide stability to the wax warmer 300.

Figure 17:
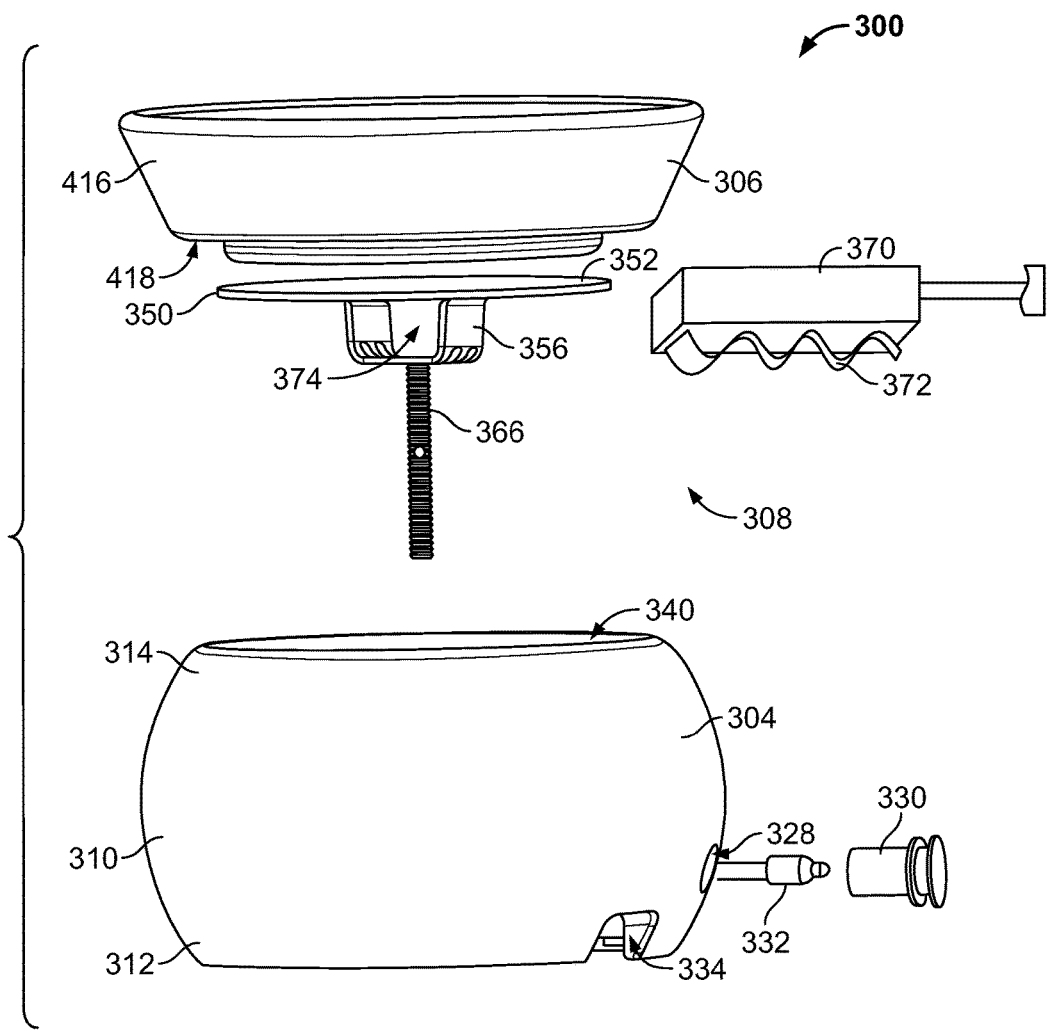
FIG. 17 is an exploded isometric view of a wax warmer.

The bottom end 312 further includes a first aperture 328 provided in the sidewall 310 (see FIG. 17). The aperture 328 is adapted to receive an indicator cover 330. The indicator cover 330 is further adapted to receive an indicator 332. Preferably, the indicator 332 is a light, e.g., a light emitting diode. However, the indicator 332 may comprise any form of visual indication means known to those of ordinary skill in the art. A second aperture 334 is also provided proximal to the bottom end 312 of the sidewall 310. Preferably, the second aperture 334 provides a pass-through for an electrical cord (not shown) in electrical communication with the indicator 332 and the heater assembly 308.

Turning again to FIG. 18, a second opening 340 is defined by the top end 314 of the sidewall 310. The second opening 340 includes a shoulder 342 extending radially inwardly from the inner surface 322 of the sidewall 310. The second opening 340 and the shoulder 342 are adapted to receive the heater assembly 308 and the reservoir 306.

It has been contemplated that the body 304 and the reservoir 306 are preferably made from a ceramic material. However, any other materials as known to those having ordinary skill in the art may be used, such as plastic, metal, stone or other natural materials, etc. The body 304 and the reservoir 306 may take any geometric shape, e.g. a square, to provide different appearances. Further, the exterior surfaces of the body 304 and the reservoir 306 may be provided with any type of surface indicia, raised patterns, or any other decorations to configure the wax warmer 300 for aesthetic purposes.

Referring to FIGS. 17-21, the heater assembly 308 includes a plate 350 having a first surface 352 and a second surface 354. A retention bracket 356 is provided on the second surface 354 of the plate 350. The retention bracket 356 includes vertical members 358 and a horizontal member 360 (see FIG. 20). In the present embodiment, the retention bracket 356 is substantially U-shaped with the open end of the U attached to the second surface 354 of the plate 350. The horizontal member 360 of the retention bracket 356 includes a first side 362 and a second side 364. A threaded rod 366 is provided on the second side 364 of the horizontal member 360 of the retention bracket 356. A heater 370 and a resilient heater clip 372 are provided within an aperture 374 of the retention bracket 356. Preferably, the resilient heater clip 372 is sized to be compressed slightly when disposed between the horizontal member 360 of the retention bracket 356 and the heater 370. The compression of the resilient heater clip 372 forces the heater 370 to remain firmly in contact with the second surface 354 of the plate 350. This arrangement of the resilient heater clip 372, the heater 370, and the plate 350 results in good thermal contact between the aforementioned structure during operation of the wax warmer 300.

In some embodiments, the threaded rod 366 may be welded to the second side 364 of the horizontal member 360. It is contemplated that the threaded rod may be attached to the second side 364 of the horizontal member 360 by any means known to those of ordinary skill in the art. For example, the threaded rod 366 may also be glued, retained with a captured nut welded to the second surface 364, or integrally formed with the horizontal member 360. This arrangement is advantageous over the prior art in that the threaded rod 366 is not in direct contact with the heater 370, thereby preventing the common manufacturing defect of over tightening the rod 366 and cracking the heater 370. Further, the heat transfer down the rod 366 is greatly reduced over the prior art so as to reduce the need for insulating caps or materials to be placed on the end of the rod.

In the present embodiment the resilient heater clip 372 is depicted with a wave-like shape. The resilient heater clip 372 includes multiple points of contact 376 with the surface of heater 370. Preferably, by including multiple points of contact 376 between the heater 370 and the resilient heater clip 372, the force from the compression of the resilient heater clip 372 is spread out over the surface of the heater 370. The present embodiment also maintains the thermal contact between the heater 370 and the plate 350. Further, this arrangement of the heater 370 and the resilient heater clip 372 is easy to assemble in a manufacturing environment.

Figure 21:
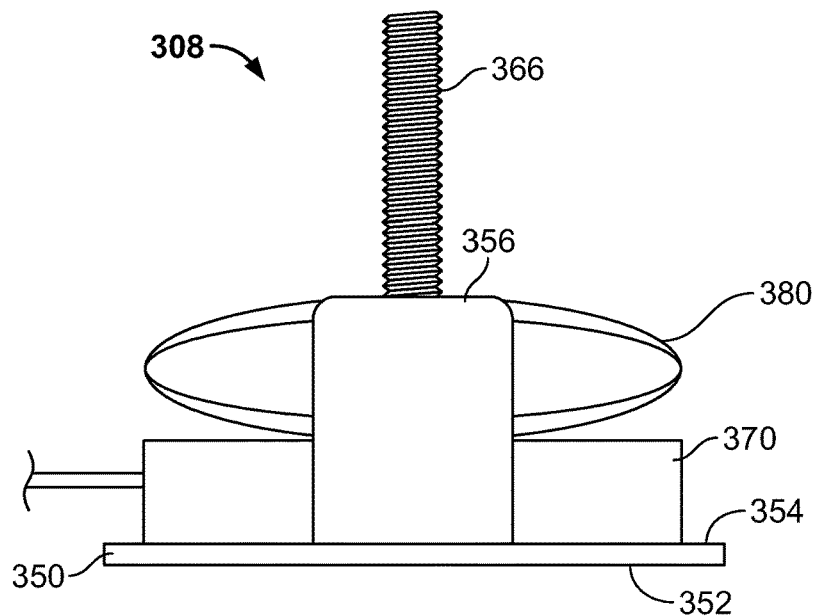
FIG. 21 is a side elevational view of a heater assembly including a second embodiment of a resilient heater clip.

Referring to FIG. 21, the heater assembly 308 includes a different embodiment of a resilient heater clip 380. The resilient heater clip 380 is substantially in the shape of an oval and placed between the heater 370 and the bracket 356 of the heater assembly 308. As with the resilient heater clip 372, the slight compression of the resilient heater clip 380 retains the heater within the bracket 356 and forces the heater 370 to maintain thermal contact with the second surface 354 of plate 350. It is contemplated that many different shapes and structures for the resilient heater clip 380 are possible by those with ordinary skill in the art.

Figure 22:
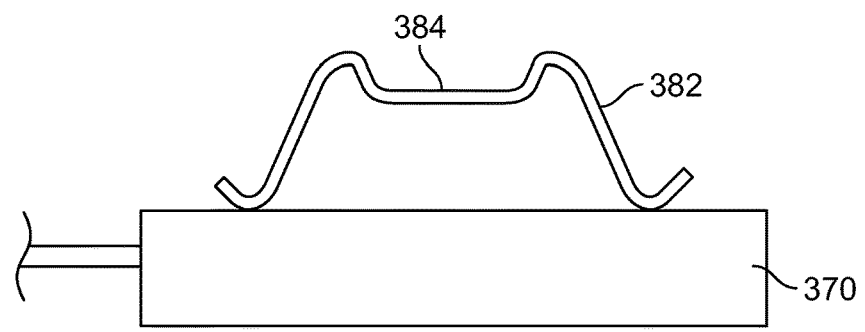
FIG. 22. is a side elevational view of a heater and a third embodiment of a resilient heater clip.

Now turning to FIG. 22, another embodiment of a resilient heater clip 382 is depicted on the heater 370. The resilient heater clip 382 includes a central recessed portion 384. The central recessed portion 384 is adapted to receive the horizontal member 360 of the retention bracket 356. The advantage of this structure is that the resilient heater clip locks into position with respect to the retention bracket 356. This aids in the assembly of the heater assembly 308 and makes the resilient heater clip self-centering with respect to the retention bracket 356. It is contemplated that the same effect of the recessed portion 384 may be achieved by welding or attaching tabs (not shown) to the resilient heater clip 382 instead of forming a recessed portion 184 by bending the material. Another alternative embodiment would be to weld or attach tabs (not shown) to the horizontal member 360, thereby creating a recessed portion (not shown) within the retention bracket 356 adapted to receive the resilient heater clip 382.

Figure 23:
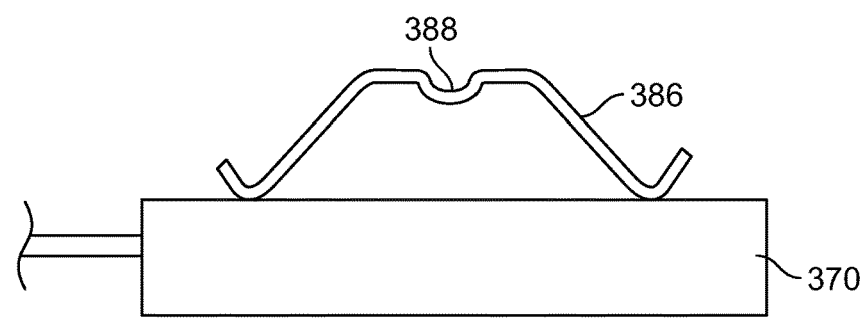
FIG. 23 is a side elevational view of a heater and a fourth embodiment of a resilient heater clip.

Now turning to FIG. 23, yet another embodiment of a resilient heater clip 386 is depicted on the heater 370. This embodiment of the resilient heater clip 386 includes a small, central recess 388 adapted to receive a detent (not shown) or protrusion (not shown) extending down from the horizontal member 360. Similar to the embodiment depicted in FIG. 22, the present embodiment may include multiple variations to accomplish similar self-centering and retention functions. For example, the central recess 388 may be a protrusion (not shown) adapted to be received in a recess (not shown) of the horizontal member 360 of the retention bracket 356.

Figure 24:
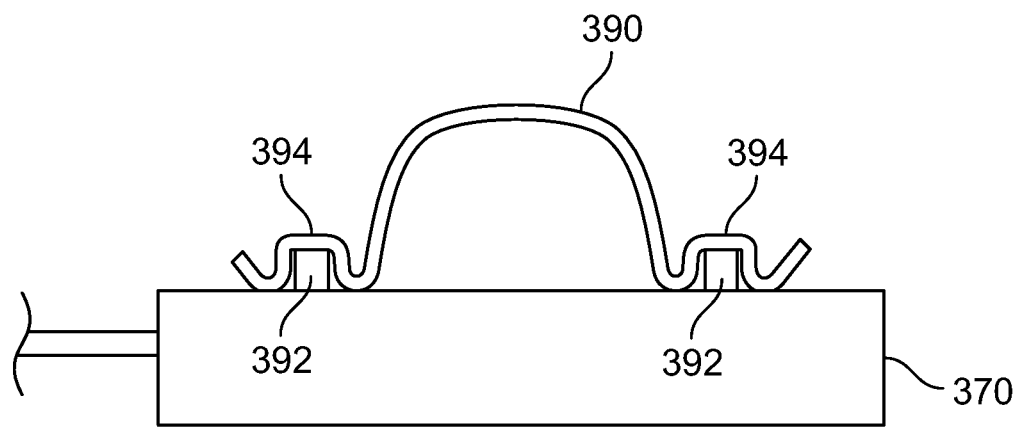
FIG. 24 is a side elevational view of a heater and a fifth embodiment of a resilient heater clip.
Figure 25:
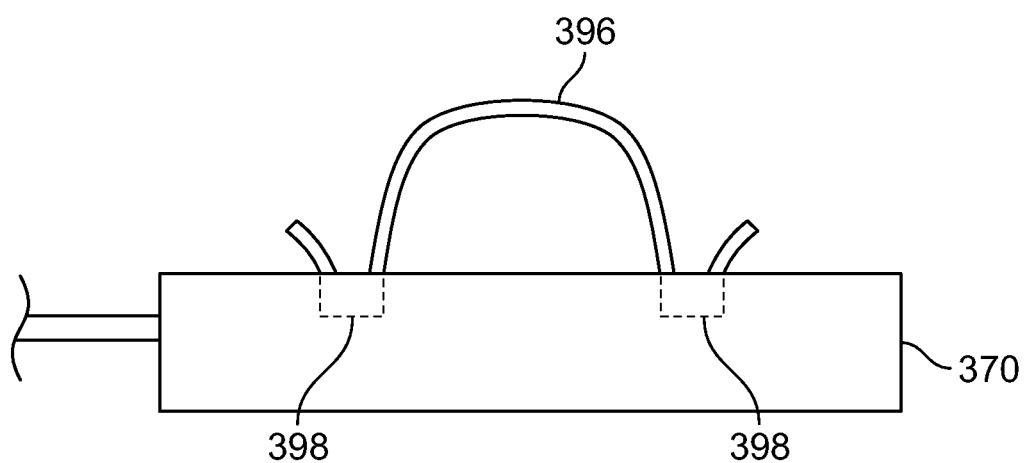
FIG. 25 is a side elevational view of a heater and a sixth embodiment of a resilient heater clip.

Now turning to FIG. 24, another embodiment of a resilient heater clip 390 is depicted on the heater 370. Ridges 392 are disposed on the heater 370. The resilient heater clip 390 includes end portions 394 adapted to receive the ridges 392. The retention of the ridges 392 within the end portions 394 maintains the location of the resilient heater clip 390 on the heater 370 during the assembly process. Now turning to FIG. 25, yet another embodiment of a resilient heater clip 396 is disposed on the heater 370. The heater 370 includes recessed portions 398 (shown with broken lines) adapted to receive the contact portions (unlabeled within the recessed portions 398). It is contemplated that one having ordinary skill in the art could design many variations of these advantageous structures to maintain the relationship between the heater 370 and the resilient heater clips 390, 396.

Figure 26:
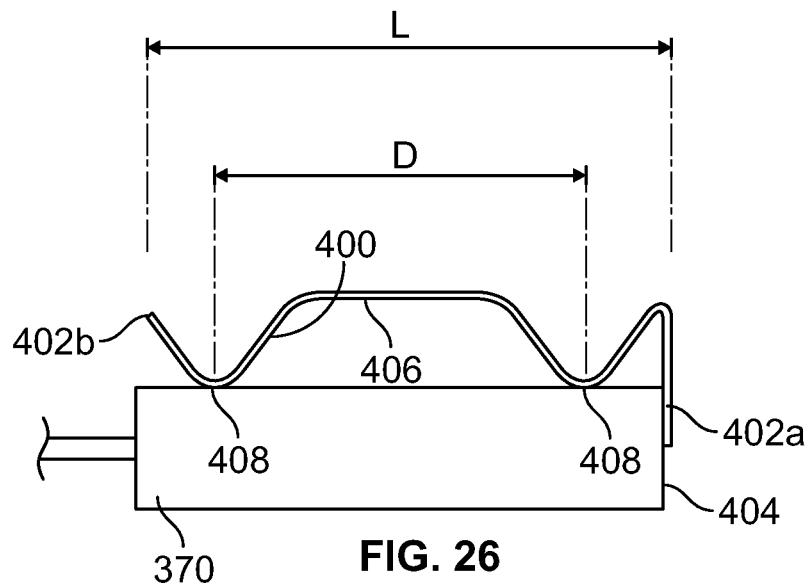
FIG. 26 is a side elevational view of a heater and a seventh embodiment of a resilient heater clip.

Now turning to FIG. 26, another embodiment of a resilient heater clip 400 is depicted on the heater 370, which may be generally characterized as being illustrative of the variations contemplated in connection with the clip. The resilient heater clip 400 includes opposing end portions 402a, 402b that may include a planar surface or an edge. In the present embodiment, 402a is represented by an elongate member disposed adjacent an end wall 404 of the heater 370. In the present embodiment, the end portion 402a assists in aligning the resilient heater clip 400 with respect to the heater 370 before being assembled into the heater assembly 308. In contrast, the end portion 402b is represented by an edge of a distal portion of the resilient heater clip 400.

The resilient heater clip 400 further includes an intermediate portion 406, which in the present embodiment may also be characterized as a medial portion. The intermediate portion 406 is generally characterized as a point of contact between the resilient heater clip 400 and the first side 362 of the retention bracket 356. In some embodiments, the intermediate portion 406 is a curved surface that contacts the bracket 356. In other embodiments, the intermediate portion 406 is a curved or angled surface that resiliently deforms from a first pre-operative state to a second operative state when it is in contact with the bracket 356, thereby deforming the intermediate portion 406 and providing a greater surface area in contact with the bracket 356. In other embodiments, the intermediate portion 406 is a flat or planar surface in contact with the bracket 356. In yet another embodiment, the intermediate portion comprises an angled surface. In fact, any geometric shape is contemplated. Further, it is also envisioned that multiple intermediate portions 406 may be provided for contact with the bracket 356, e.g., 2, 3, 4, 5, 6, or any number of intermediate portions. It is further contemplated that the intermediate portion 406 may include structural elements adapted to retain the resilient heater clip 400 and the heater 370 in the retention bracket 356. For example, the intermediate portion 406 may include a U-shaped indentation sized appropriately to receive the horizontal member 360 of the retention bracket 356 to prevent lateral movement of the resilient heater clip 382 and the heater 370 after assembly.

The resilient heater clip 400 also includes several heater contact portions 408, which may similarly comprise curved, angled, or planar sections as noted in connection with the intermediate portion 406. In fact, the contact portions 408 may also be provided with a curved or angled surface that resiliently deforms from a first pre-operative state to a second operative state when it is in contact with the heater 370. Further, other contact portions 408 may comprise other curved, angled, or flat surfaces that may be used to provide contact with the heater 370. Other embodiments may have more than one contact portion 408 provided, e.g., 2 contact portions, or 3, 4, 5, 6, or any number of contact portions. The utilization of additional contact portions 408 optimizes the transfer of force from the resilient heater clip 400 to the heater 370 to protect against breakage.

When the resilient heater clip 400 is assembled within the aperture 374 of the retention bracket 356, the intermediate portion(s) 406 is in contact with the first side 362 of the retention bracket 356. In turn, the force is transferred through the resilient heater clip 400 to the heater 370 at the contact portions 408. The distance between first and second contact portions may be generally described as D. Preferably, the distance D defines a void between opposing contact portions 408, i.e., an area and/or length where the resilient heater clip 400 does not contact the heater 370. In the instance where more than two contact portions 408 are provided, the distance D and D' may be identical or different, wherein each distance D and D' similarly defines a void. The overall shape of the resilient heater clip is of a non-uniformly planar structure, with a straight line length of the resilient heater clip 400 represented by a length L. The non-bent or total length of the resilient heater clip 400 is represented by a length T, wherein T>L. In some embodiments, the ratio of L:T is between about 0.5 to about 0.95.

The resilient heater clips 372, 380, 382, 386, 390, 396, and 400 of the present embodiments may be constructed out of any appropriate material known to one having ordinary skill in the art. For example, spring steel that is ¾ or fully hardened is a material that exhibits the required resiliency properties at elevated temperatures. Some other examples may be brass, copper, or high temperature plastics and resins. It is also contemplated that the resilient heater clips 372, 380, 382, 386, 390, 396, and 400 may take on alternative forms of resilient members. For example, a wire spring or a coil spring may be modified by one having ordinary skill in the art to incorporate the features presented herein to achieve the desired benefits. It is also contemplated that the aforementioned resilient heater clips may be attached to the heater 370 or the retention bracket 356 by any number of means known to those of ordinary skill in the art. Some examples are welding, brazing, mechanical means such as rivets, nuts and bolts, screws, adhesives and resins, and tape.

In some embodiments, the heater 370 is a resistive type heater. In other embodiments, the heater 370 is other types of heaters. For example, the heater may be a positive thermal coefficient heater or an inductive type heater. It is further contemplated that the heater 370 may be replaced by a series of heaters and resilient heater clips disposed on the second surface 354 of the plate 350.

Figure 27:
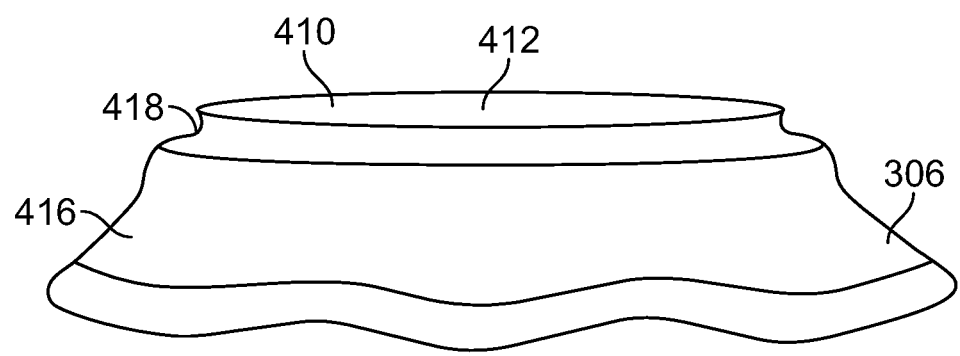
FIG. 27 is a bottom perspective view of another reservoir.

Turning to FIGS. 18 and 27, the reservoir 306 includes a bottom wall 410 having a first surface 412 and a second surface 414. The reservoir 306 further includes a sidewall 416. The bottom wall 410 and the sidewall 416 form a cup-like structure for containing the wax melt 302 in a pre-operative solid state and in an operative state when the wax melt 302 is in a liquid or semi-liquid state. The reservoir 306 further includes a cut-out 418. The shoulder 342 and the second opening 340 of the body 304 are configured to receive the plate 350 of the heating assembly 308 and the cut-out 418 of the reservoir 306. The first surface 412 of the reservoir 306 is generally flat to provide maximum thermal contact with the plate 350. The interaction of the cut-out 418 of the reservoir 306 and the shoulder 342 of the second opening 340 of the body 304 assists in retaining the reservoir 306 on the body 304. The present arrangement also ensures that the reservoir 306 is centered on the heater assembly 308 for improved thermal transfer from the heater 370 to the wax melt 302.

The wax warmer 300 in the embodiments depicted herein may be assembled quickly and efficiently. A wire harness (not shown) is first connected to the heater 370, the indicator 332, and an electrical power source (not shown). Preferably, the electrical power source is an electrical cord adapted to be plugged into an electrical socket. It is contemplated that the electrical power source may be batteries (not shown) contained within the body 304. It is further contemplated that any suitable electrical power source known to those having ordinary skill in the art may suffice. The next step in assembly is to insert the heater 370 and the resilient heater clip 372 into the retention bracket 356. The indicator 332 may then be inserted into the indicator cover 330. Next, the wire harness (not shown) and the heater assembly 308 may be inserted into the second opening 340. The threaded rod 366 is sized to extend through the interior space 316 of body 304 and through an opening 420 in base plate 326. A locking-nut 422 secures the threaded rod 366 to the base plate 326. In some embodiments, an electrical cord (not shown) extends through the second aperture 334. As depicted in FIG. 18, the assembled wax warmer 300 includes a reservoir in thermal contact with a plate 350. The plate 350 is in thermal contact with the heater 370. The heater 370 is retained within the bracket 356 by the compression of the resilient heater clip 372. The heater assembly 308 is retained within the second opening 340 of the body 304 by the threaded rod 366 extending through the base plate 326 and secured by the locking-nut 422.

The wax melt 302 is wickless and may comprise any geometric shape. In some embodiments, the wax melt 302 has a generally square shape with slightly rounded curvature imparted thereto at an area where sidewalls of the wax melt intersect with each other. There are no substantial surface interruptions beyond minor surface irregularities formed during the manufacturing process. It is contemplated that the shape of the wax melt 302 may be configured to be beneficial for manufacturing purposes or aesthetic reasons or both.

Any of the embodiments described herein may be modified to include any of the structures or methodologies disclosed in connection with different embodiments. Further, the present disclosure is not limited to wax warmers of the type specifically shown. Still further, the wax warmers of any of the embodiments disclosed herein may be modified to work with any type of warmers that utilize wax melts or the like.

Figure 28:
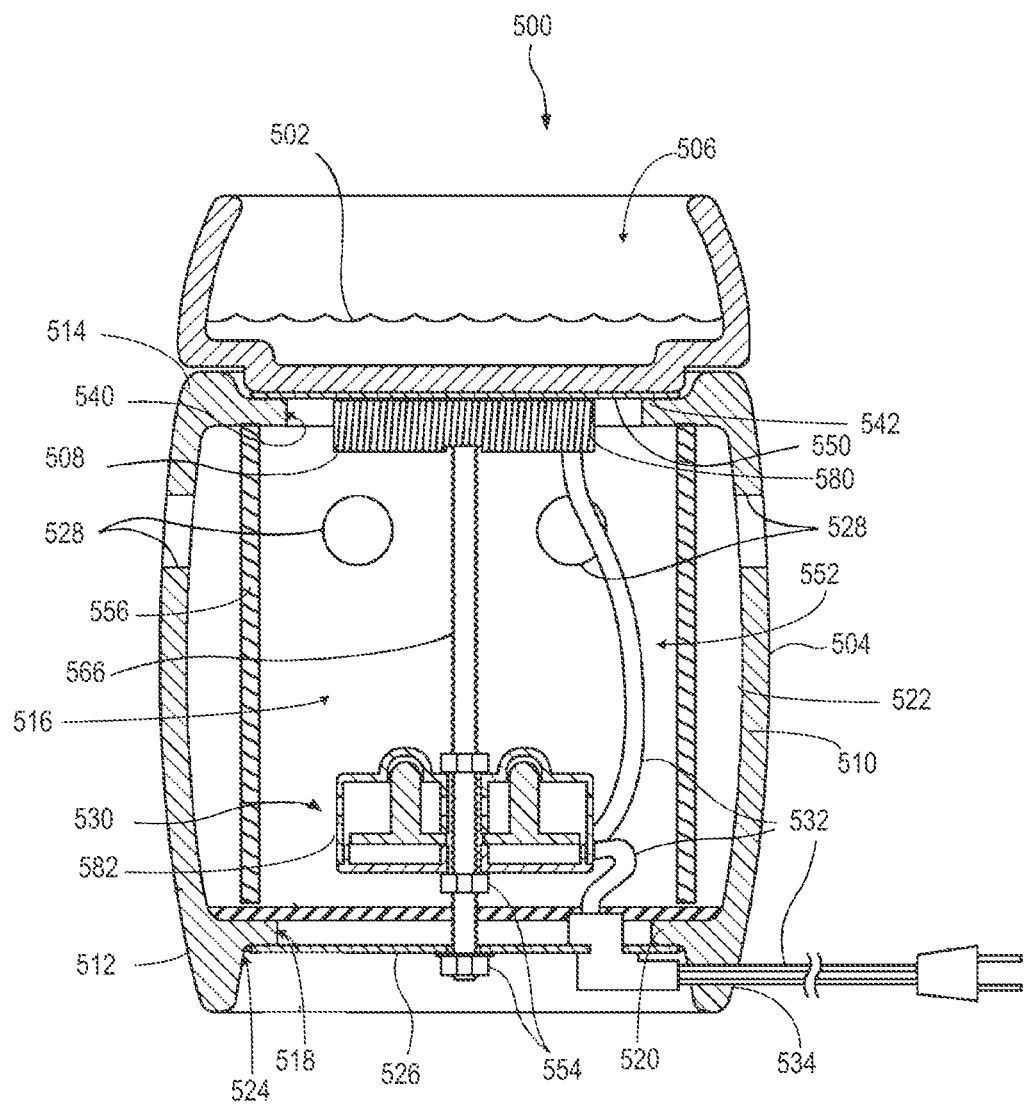
FIG. 28 is a cross-sectional side elevational view of yet another wax warmer.

Referring to FIG. 28, yet another wax warmer 500 is depicted. The wax warmer 500 is designed to heat a wax melt 502 and thereby release a fragrance or other material contained therein into the surrounding environment. The wax warmer 500 generally includes a body 504, a reservoir 506, and a heater assembly 508. The body 504 is fashioned to house the heater assembly 508 and provide a support structure for the reservoir 506. The wax warmer 500 is generally described to include the aforementioned components, but the wax warmer 500 may be adapted to add or remove various components according to specific user requirements.

Still referring to FIG. 28, the body 504 includes a sidewall 510 having a bottom end 512 and a top end 514. In the present embodiment, the sidewall 510 is generally cylindrical in shape and defines an interior space 516. The bottom end 512 defines a first opening 518. A lip 520 extends from an inner surface 522 of the sidewall 510. The bottom end 512 and the lip 520 form a recess 524 adapted to receive a base plate 526 that is disposed adjacent the bottom end 512 of the body 504. Portions of the bottom end 512 of the body 504 may include extensions (not shown) or other structures (feet, pads, structures with high coefficients of friction, etc.) generally known to those having ordinary skill in the art to provide stability to the wax warmer 500.

The sidewall 510 further includes one or more apertures 528 provided therein. The apertures 528 may be adapted to receive a light emissive or transmissive cover (not shown) and/or an indicator, such as an LED, or sensor (not shown). For example, the apertures 528 may allow light, provided by an electrical light source 530, from the interior space 516 to be visible through the apertures 528. Additionally, one or more of the apertures 528 may be fully or partially unobstructed to facilitate cooling of the body 504 and/or the flow of air through the interior space 516 of the wax warmer 500. The apertures 528 may be any desired shape and size for aesthetics, cooling, and light passage. For example, and without limitation, the apertures 528 may be circular (as shown in FIG. 28), triangular, rectangular, polygonal, star-shaped, crescent-shaped, irregularly-shaped, flower-shaped, etc. A second aperture 534 is also provided proximal to the bottom end 512 of the sidewall 510. Preferably, the second aperture 534 provides a pass-through for an electrical cord 532 in electrical communication with the electrical light source 530 and the heater assembly 508.

Referring still to FIG. 28, a second opening 540 is provided at the top end 514 of the sidewall 510. The second opening 540 is bounded by a shoulder 542 extending radially inwardly from the inner surface 522 of the sidewall 510. The second opening 540 and the shoulder 542 are adapted to receive the heater assembly 508 and the reservoir 506.

It has been contemplated that the body 504 and the reservoir 506 are preferably made from a ceramic material. However, any other materials as known to those having ordinary skill in the art may be used, such as plastic, metal, stone or other natural materials, etc. However, any other materials as known to those having ordinary skill in the art may be used, such as plastic, metal, stone or other natural materials, etc. The body 504 and the reservoir 506 may take any geometric shape, e.g. a square, to provide different appearances. Further, the exterior surfaces of the body 504 and the reservoir 506 may be provided with any type of surface indicia, raised patterns, or any other decorations to configure the wax warmer 500 for aesthetic purposes.

With continued reference to FIG. 28, an electrical assembly 552 of the wax warmer 500 described above may be at least partially disposed within the interior space 516 of the body 504. The electrical assembly 552 may include the heater assembly 508 and the electrical light source 530. In some embodiments, structural components may hold some of the various components in place. For example, a threaded rod 566 may extend through the base plate 526 and the electrical light source 530 and may abut against the heater assembly 508. At least one nut 554 may hold the threaded rod 566 and the various components in place.

The heater assembly 508 may be positioned within the body 504 proximate the second opening 540 such that the heater assembly 508 may heat the wax melt 502 in the reservoir 506. In some embodiments, the electrical light source 530 may be positioned within the body 504 at a location distant to that of the heater assembly 508, such as proximate the first opening 518 of the bottom end 512. In other embodiments, the electrical light source 530 may be positioned within the body 504 at a location proximate the heater assembly 508. The heater assembly 508 may be a heat source such as a resistance heater, an incandescent light bulb, a PTC heater, or any other heater known to one in the art.

In some embodiments, the wax warmer 500 includes a top plate or plate 550 under the reservoir 506. The plate 550 may support the reservoir 506 on the body 504. The top plate 550 may be formed from a metallic material and disposed adjacent the top end 514 of the body 504. The heater assembly 508 may be abutted against or otherwise thermally coupled to a surface of the top plate 550. By way of non-limiting examples, the heater assembly 508 may be coupled to the top plate 550 with an adhesive, with a mechanical connection (e.g., a clip, screw, interference fit, etc.), by being pushed against the top plate 550 with the threaded rod 566 (as shown), or any combination thereof. Thus, in some embodiments, the plate 550 interposes the reservoir 506 and the heater assembly 508. In embodiments in which the reservoir 506 and the body 504 are separate and detachable, the top plate 550 may be attached to one of the reservoir 506 or the body 504 or neither. In some embodiments, the wax warmer 500 may not include the top plate 550. In such embodiments, the heater assembly 508 may abut directly against a bottom of the reservoir 506.

Figure 29:
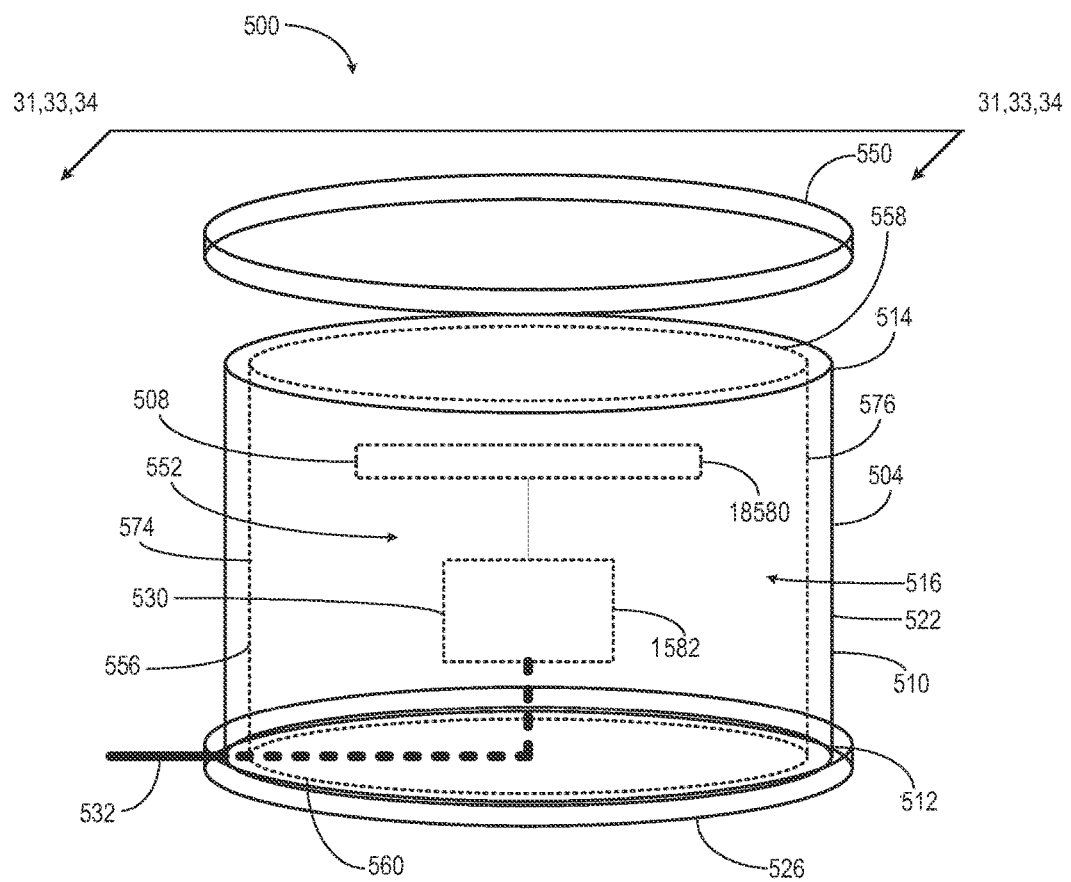
FIG. 29 is a schematic view of a wax warmer with an electrical barrier.

Turning now to FIG. 29, a simplified schematic diagram of the wax warmer 500 is shown. The wax warmer 500 includes substantially the same components as described with reference to FIG. 28, therefore similar reference numerals will be used.

Figure 36:
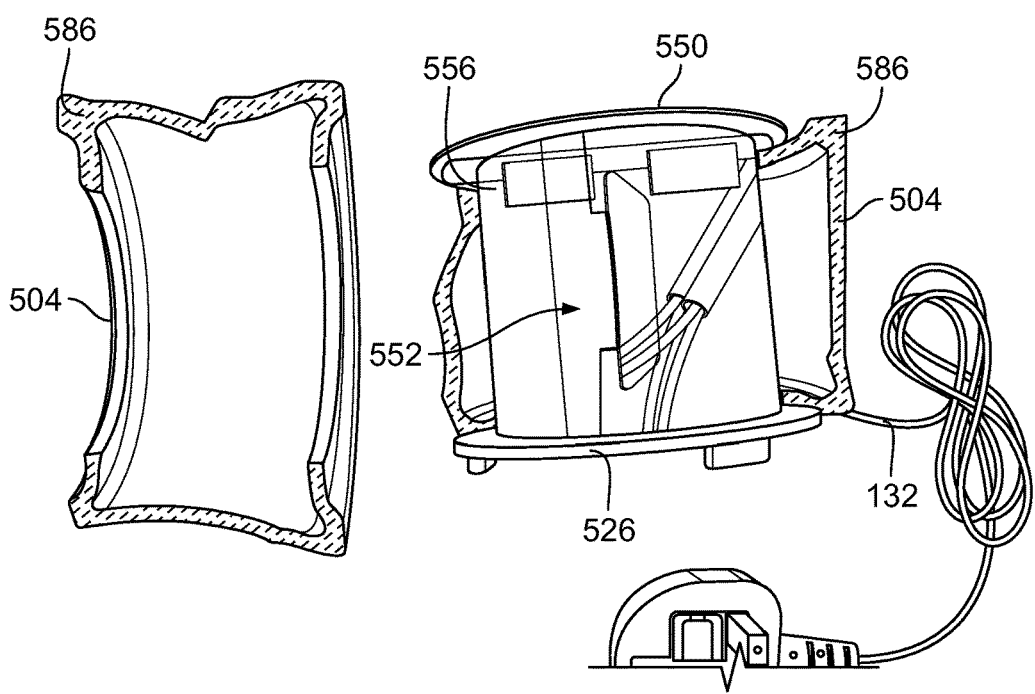
FIG. 36 is an image of the wax warmer of FIG. 35 after the ball impact test showing an electrical barrier.

An electrical barrier 556 is positioned inside the body 504 of the wax warmer 500 in the embodiment shown in FIG. 29 (see also FIG. 28). The electrical barrier 556 may take the form of an annular sleeve, for example, and surround the electrical assembly 552. Thus, if the body 504 of the wax warmer 500 is damaged or broken, as shown in FIG. 36, the electrical assembly 552, including the heater assembly 508 and electrical light source 530, are not exposed to a user of the wax warmer 500. In addition, the electrical barrier 556 ensures that the wax warmer 500 is in compliance with standards related to air fresheners and deodorizers, such as the UL 283 standard, as will be described in further detail below.

Figure 30A:
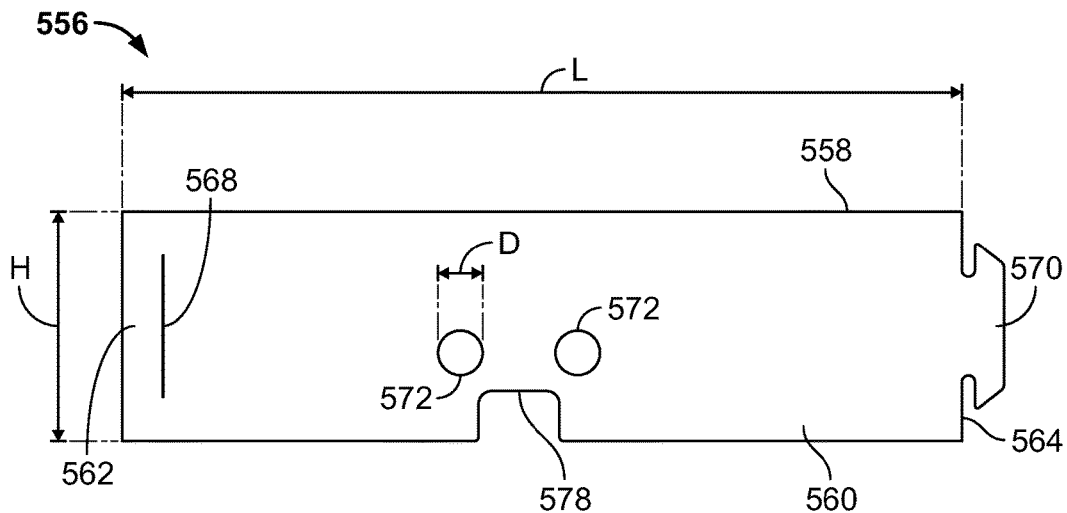
FIG. 30A is a side elevational view of an electrical barrier layout according to one embodiment of the disclosure.
Figure 30B:
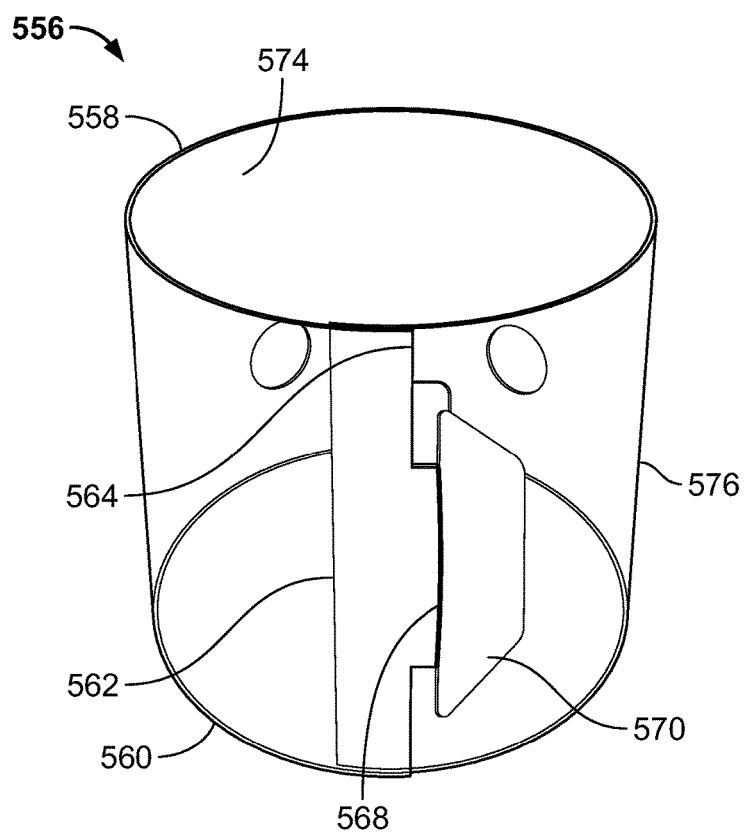
FIG. 30B is a perspective view of the electrical barrier of FIG. 30A coupled together to form a generally cylindrical shape.

A first embodiment of the electrical barrier 556 is shown in FIGS. 30A and 30B. The electrical barrier 556 can begin as a flat, substantially rectangular layout, as shown in FIG. 30A having a length dimension L and a height dimension H. The length dimension L and the height dimension H may vary depending on the dimensions of the particular wax warmer 500 the electrical barrier 556 is used in. In some embodiments, the length dimension L is about 22.5 centimeters, and the height dimension H is about 5.7 centimeters. The electrical barrier 556 may have a thickness dimension T (see FIG. 31) that is preferably between about 0.025 centimeters and about 0.15 centimeters. However, the length dimension L may be any suitable length to allow the electrical barrier 556 to fit within the body 504 of the wax warmer 500. Similarly, the height dimension H may be of any height to allow the electrical barrier 556 to fit within the body 504 and not extend beyond the base plate 526 or the top plate 550 of the wax warmer 500. Likewise, the thickness dimension T may vary depending on the specific wax warmer 500 that the electrical barrier 556 is used in. For example, depending on the heater assembly 508 used in a particular wax warmer 500, the thickness dimension T may change in order to withstand a variety of heat outputs.

Turning again to FIG. 30A, the electrical barrier 556 includes a top edge 558 and a bottom edge 560 that extend the length dimension L. In the present embodiment, the top edge 558 is parallel to the bottom edge 560. A first side edge 562 and a second side edge 564 extend about the height dimension H. In the present embodiment, the first and second side edges 562, 564 are substantially parallel to one another. A groove 568 is provided adjacent to the first side edge 562, and a tongue portion 570 is provided adjacent to the second side edge 564. As shown in FIG. 30B, the groove 568 is configured to receive the tongue portion 570 to form a substantially cylindrical electrical barrier 556. Alternatively, the first side edge 562 and the second side edge 564 may be heat sealed, adhered, or coupled together using any suitable mechanical fastener (e.g., a staple or a rivet). In yet another alternative embodiment, the first side edge 562 and the second side edge 564 may be integrally molded together to form the electrical barrier 556.

Figure 31:
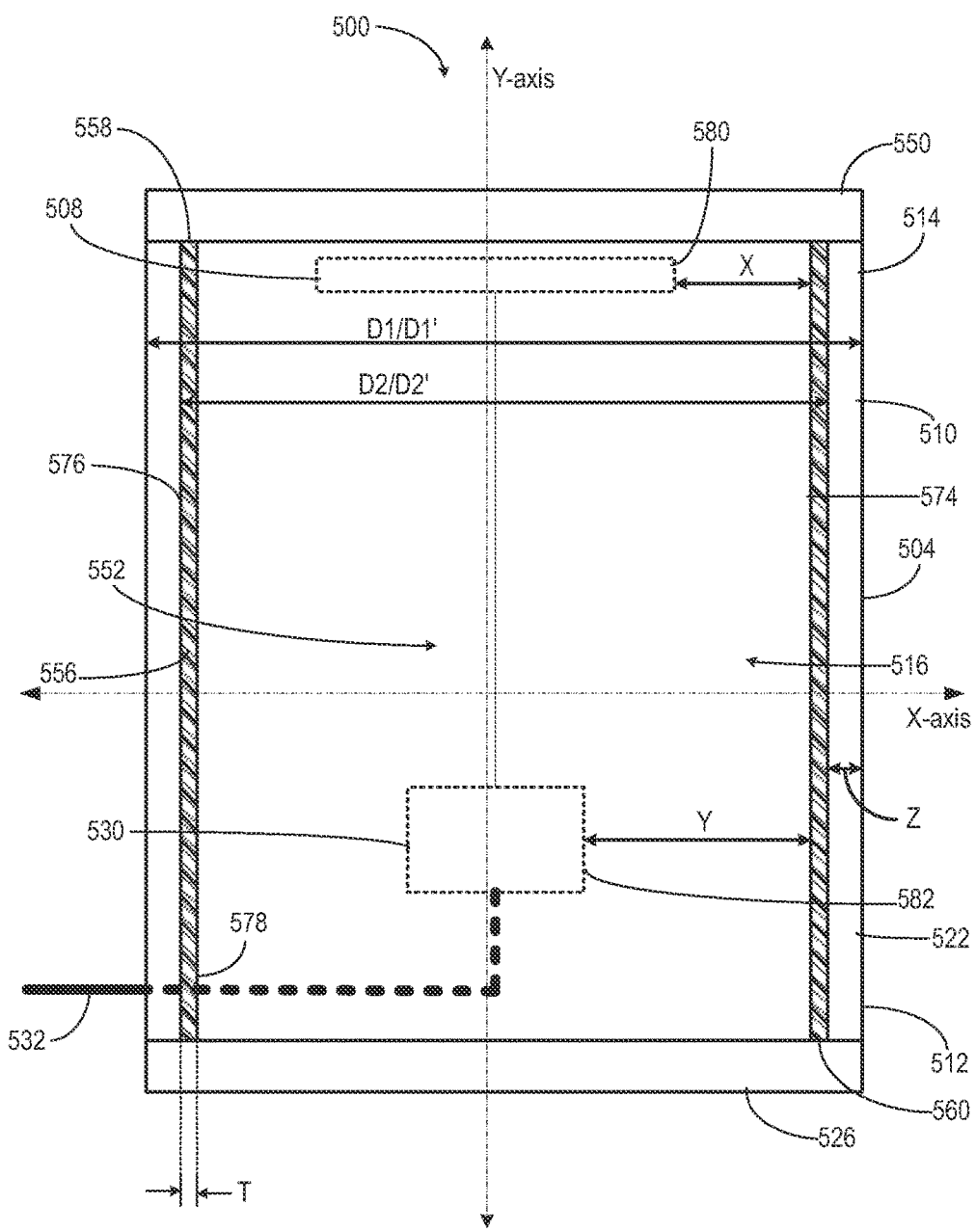
FIG. 31 is a cross-sectional view of the wax warmer taken generally along the line 31-31 of FIG. 29 with the electrical barrier in a first position.

In some embodiments, the electrical barrier 556 may take the form of a sleeve that has a substantially circular cross-section when taken through a horizontal axis (X-axis in FIG. 31). In other embodiments, the horizontal cross-section of the electrical barrier 556 is oval, circular, curvilinear, triangular, or any suitable shape in order to shield the electrical assembly 552. In the embodiment shown in FIGS. 30A and 30B the electrical barrier 556 is a right circular cylinder. However, the electrical barrier 556 can also take the form of an elliptic cylinder, an oblique cylinder, a parabolic cylinder, a hyperbolic cylinder, etc.

Still referring to FIGS. 30A and 30B, the electrical barrier 556 may include one or more apertures 572 that extend from an interior surface 574 to an exterior surface 576 of the electrical barrier 556. The one or more apertures 572 may include a diameter D that is not to exceed 0.95 centimeters. In other embodiments, the diameter D of the one or more apertures 572 is between about 0.64 centimeters and about 0.95 centimeters. A maximum diameter D is established such that in the event the body 504 of the wax warmer 500 is broken or damaged, a user is inhibited from contacting any of the components of the electrical assembly 552. Or, alternatively, during a standardized ball impact test, a finger probe (not shown) is inhibited from contacting any of the components of the electrical assembly 552 to maintain compliance with the UL 283 standard, for example.

The purpose of the one or more apertures 572 disposed on the surfaces 574, 576 of the electrical barrier 556 is to allow light, provided by the electrical light source 530, to be visible through the apertures 528 on the body 504. Additionally, the apertures 572 may facilitate cooling of the body 504 as heated air builds up within the interior space 516 during use of the wax warmer 500. The apertures 572 may be any desired shape for aesthetics, cooling, and light passage. The electrical barrier 556 may further include a slot 578, as shown in FIG. 30A, disposed along the bottom edge 560 of the electrical barrier 556. The slot 578 may be substantially sized so as to provide a passage for the electrical cord 532 to pass through the electrical barrier 556 and through the second aperture 534 (see FIG. 28) of the body 504.

Figure 32A:
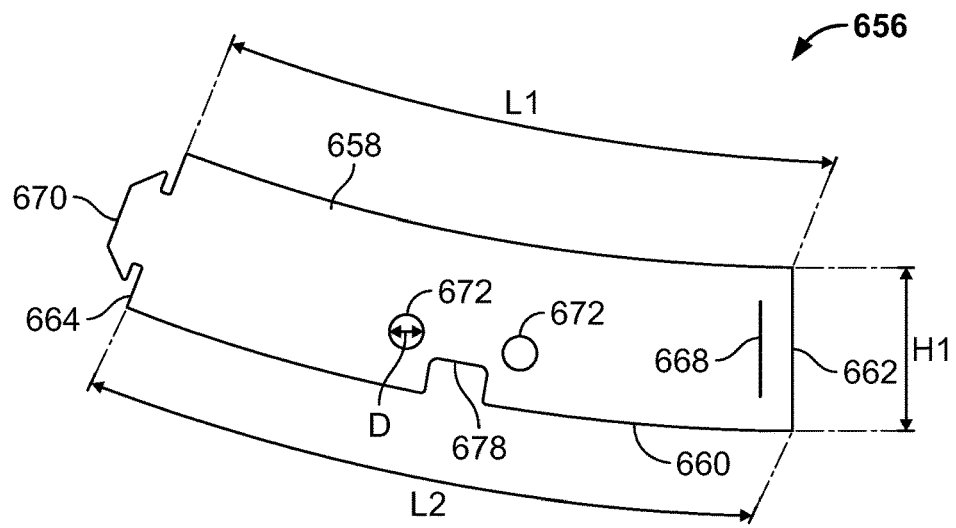
FIG. 32A is a side elevational view of an electrical barrier layout according to another embodiment of the disclosure.
Figure 32B:
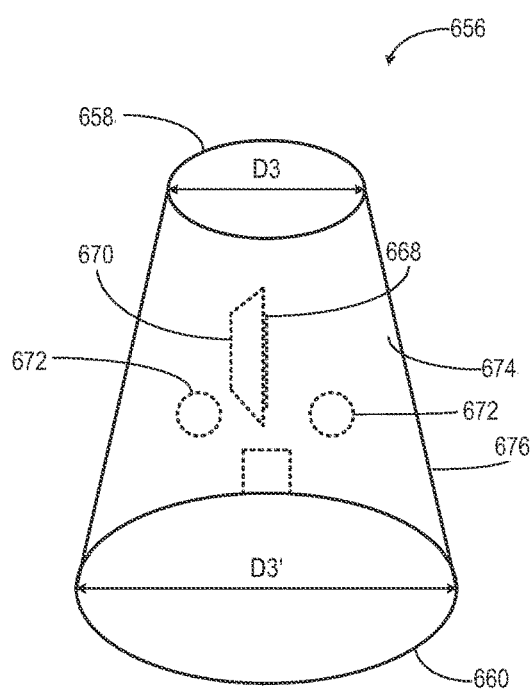
FIG. 32B is a perspective view of the electrical barrier of FIG. 32A coupled together to form a generally frusto-conical shape.

In an alternative embodiment, as shown in FIGS. 32A and 32B, a non-cylindrical electrical barrier 656 is provided that is substantially frusto-conical shaped. Similar to the cylindrical shaped electrical barrier 556, the frusto-conical shaped electrical barrier 656 can begin as a flat layout, as shown in FIG. 32A. Because the electrical barrier 656 is frusto-conical shaped, the top edge 658 may be slightly curved and have a length dimension L1, and the bottom edge 660 may also be slightly curved and have a length dimension L2. The length dimension L1 is measured as a curved line from the first side edge 662 to the second side edge 664 along the top edge 658. Similarly, the length dimension L2 is measured as a curved line from the first side edge 662 to the second side edge 664 along the bottom edge 660. Thus, the length dimension L1 is less than the length dimension L2. In some embodiments, the length dimension L1 is about 20.9 centimeters, and the length dimension L2 is about 22.5 centimeters. The electrical barrier 656 also includes a height dimension H1 along the first side edge 662 and the second side edge 664 that is about 5.7 centimeters. The height dimension H1 is measured from the top edge 658 to the bottom edge 660 along either of the side edges 662, 664. The length dimensions L1 and L2 and the height dimension H1 may vary depending on the dimensions of the particular wax warmer 500 the electrical barrier 656 is used in. Thus, the length dimensions L1 and L2 may be any suitable length to allow the electrical barrier 656 to fit within the body 504 of the wax warmer 500. Similarly, the height dimension H1 may be of any height to allow the electrical barrier 656 to fit within the body 504 and not extend beyond the base plate 526 or the top plate 550. The electrical barrier 656 may have a thickness dimension (not shown) that is substantially the same as the thickness dimension T (see FIG. 31) of the cylindrical electrical barrier 556.

Due to the varying length dimensions L1 and L2, the frusto-conical shaped electrical barrier 656 has a minor diameter D3 at the top edge 658 that is less than a major diameter D3' at the bottom edge 660 (see FIG. 32B). In one embodiment, the minor diameter D3 is about 6.4 centimeters, and the major diameter D3' is about 6.7 centimeters. In contrast, the cylindrical shaped electrical barrier 556, as shown in FIG. 31, includes a uniform diameter D2 at the top end 514 and the bottom end 512 of the wax warmer 500 (see FIG. 31). The diameter D2 may be, in one embodiment, at least about 5.7 centimeters. However, the minor and major diameters D3 and D3', and the diameter D2, can vary depending on the aesthetic design, for example, of the wax warmer 500. Thus, the minor and major diameters D3 and D3' and the diameter D2 may be any suitable size to allow the frusto-conical shaped electrical barrier 656 or the cylindrical shaped electrical barrier 556 to fit within the body 504 of the wax warmer 500.

Referring again to FIGS. 32A and 32B, a groove 668 may be provided adjacent to the first side edge 662, and a tongue portion 670 may be provided adjacent to the second side edge 664. As shown in FIG. 32B, the groove 668 is configured to receive the tongue portion 670 to form the substantially frusto-conical shaped electrical barrier 656. Alternatively, the first side edge 662 and the second side edge 664 may be heat sealed, adhered, or coupled together using any suitable mechanical fastener (e.g., a staple or a rivet). In yet another alternative embodiment, the first side edge 662 and the second side edge 664 may be integrally molded together to form the electrical barrier 656.

Still referring to FIGS. 32A and 32B, the electrical barrier 656 may include one or more apertures 672 that extend from an interior surface 674 to an exterior surface 676 of the electrical barrier 656. The one or more apertures 672 may include a diameter D that is not to exceed 0.95 centimeters for the same reasons as previously described. In other embodiments, the diameter D of the one or more apertures 672 is between about 0.64 centimeters and about 0.95 centimeters.

The electrical barriers 556 and 656 of the present embodiments may be constructed of a polymeric material (e.g., polycarbonate, polypropylene, etc.), a mica material, or a horizontal burning (HB) material, for example. In some embodiments, the electrical barriers 556 and 656 may be constructed of any suitable flexible material. However, it is contemplated that a rigid material, such as a mica material, may be used for the electrical barriers 556 and 656.

The material of the electrical barriers 556 and 656 preferably includes a specific melting temperature above the maximum heat output of the heater assembly 508 used within the wax warmer 500. More preferably, the material of the electrical barriers 556 and 656 has a specific melting temperature above the combined heat output of the electrical assembly 552, which may include one or more of a heater(s), a light(s), a sensor(s), or other electrical component(s) capable of outputting heat. Therefore, the electrical barriers 556 and 656 preferably have a melting temperature between about 350 degrees Fahrenheit and about 510 degrees Fahrenheit. For example, in one non-limiting embodiment, the electrical light source 530 may provide a heat output ranging from about 10 watts to about 20 watts. Similarly, the heater assembly 508 may include a resistive heater, which has a heat output ranging from about 10 watts to about 20 watts.

Turning now to FIG. 31, the electrical barrier 556 is shown positioned within the body 504 of the wax warmer 500 and surrounding the electrical assembly 552. In some embodiments, the electrical barrier 556 is positioned a distance X from the electrical assembly. In the present scenario, the distance X may be defined as the distance from the interior surface 574 of the electrical barrier 556 to an exterior surface 580 of the heater assembly 508. The distance X may be measured in a horizontal plane defined by the X-axis shown in FIG. 31. Additionally, or alternatively, the electrical barrier 556 is positioned a distance Y from the electrical light source 530. The distance Y may be defined as the distance from the interior surface 574 of the electrical barrier 556 to an exterior surface 582 of the electrical light source 530. The distance Y may also be measured in a horizontal plane defined by the X-axis shown in FIG. 31. In one embodiment, the distance Y is 0.5 centimeters. In some embodiments, the distance X is a minimum distance of about 0.3 centimeters. In some embodiments, however, minimum distances for X and Y may vary depending on the specific heater assembly 508 or electrical light source 530 used in the wax warmer 500.

The minimum distances X and Y may, in some embodiments, be directly correlated to a ratio of the heat output of the heater assembly 508 or the electrical light source 530 (as measured in watts) to the predetermined melting temperature (as measured in degrees Fahrenheit) of the material of the electrical barrier 556. In some embodiments, the ratio of the heat output to the predetermined melting temperature is between about 0.02 and 0.05. Thus, the higher the heat output produced by either the heater assembly 508 or the electrical light source 530, the greater the distance X and/or Y will be.

In some embodiments, the electrical barriers 556 and 656 may be comprised of 100% polymeric materials, which may include one or more materials, and have a thermal rating of at least 230 degrees Fahrenheit and a modulus of elasticity of between 1.5 GPa and 2.6 GPa. Further, in this contemplated embodiment, the electrical barrier 556, 656 has a diameter, or minor diameter, of at least 5.7 centimeters Still referring to FIG. 31, the electrical barrier 556 may be positioned a distance Z from the sidewall 510 of the body 504. The distance Z may be measure from the exterior surface 576 of the electrical barrier 556 to the inner surface 522 of the sidewall 510. In an alternative embodiment, the electrical barrier 556 may be in direct contact with the inner surface 522 of the sidewall 510. However, regardless of the distance Z, the diameter D2 of the electrical barrier 556 is less than a diameter D1 of the body 504 to allow the electrical barrier 556 to be positioned within the body 504. Similarly, with reference to the frusto-conical shaped electrical barrier 656 (see FIGS. 32A and 32B), the diameters D3 and D3' are less than the diameter D1 of the body 504.

Figure 33:
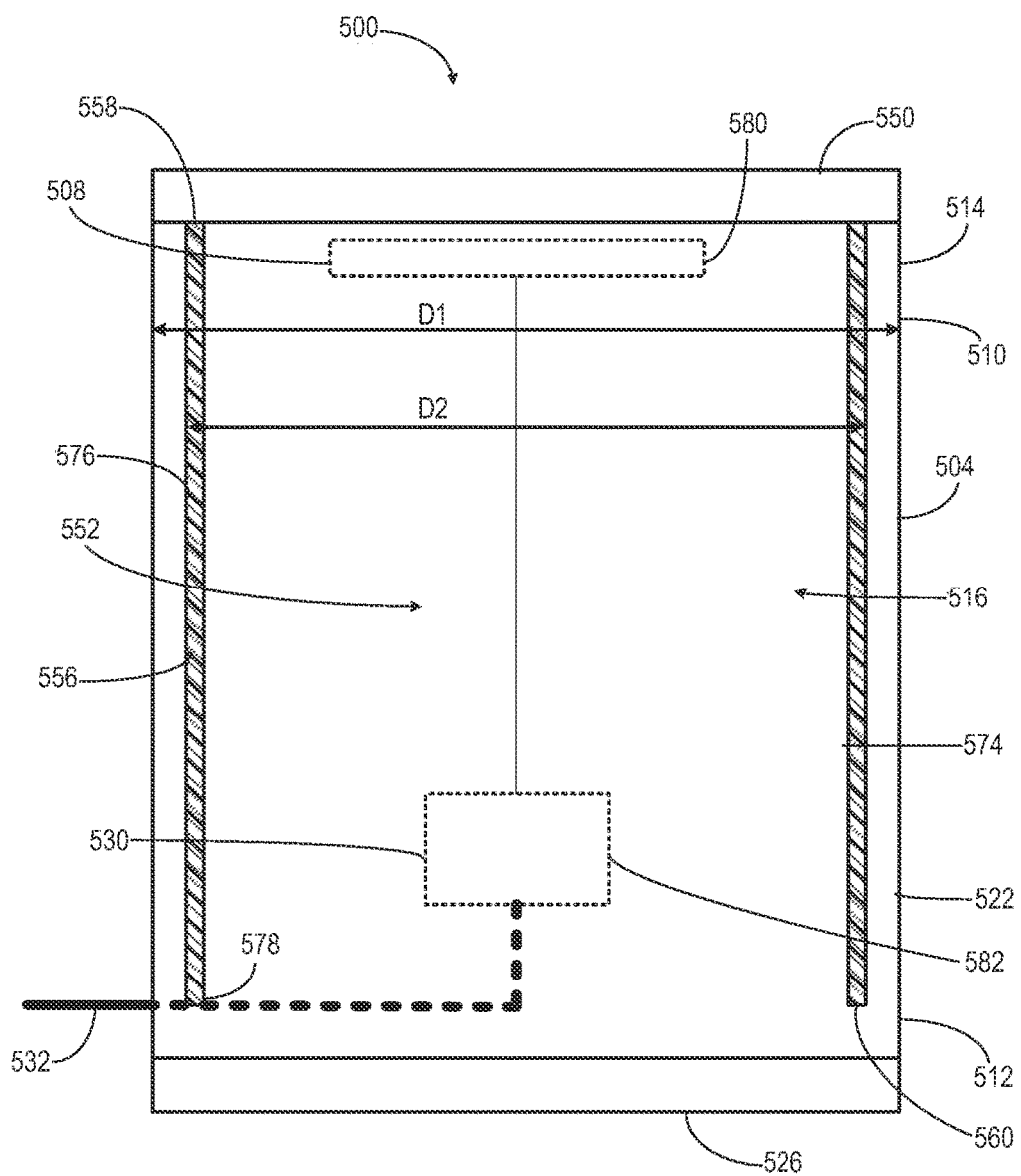
FIG. 33 is a cross-sectional view of the wax warmer taken generally along the line 33-33 of FIG. 29 with the electrical barrier in a second position.
Figure 34:
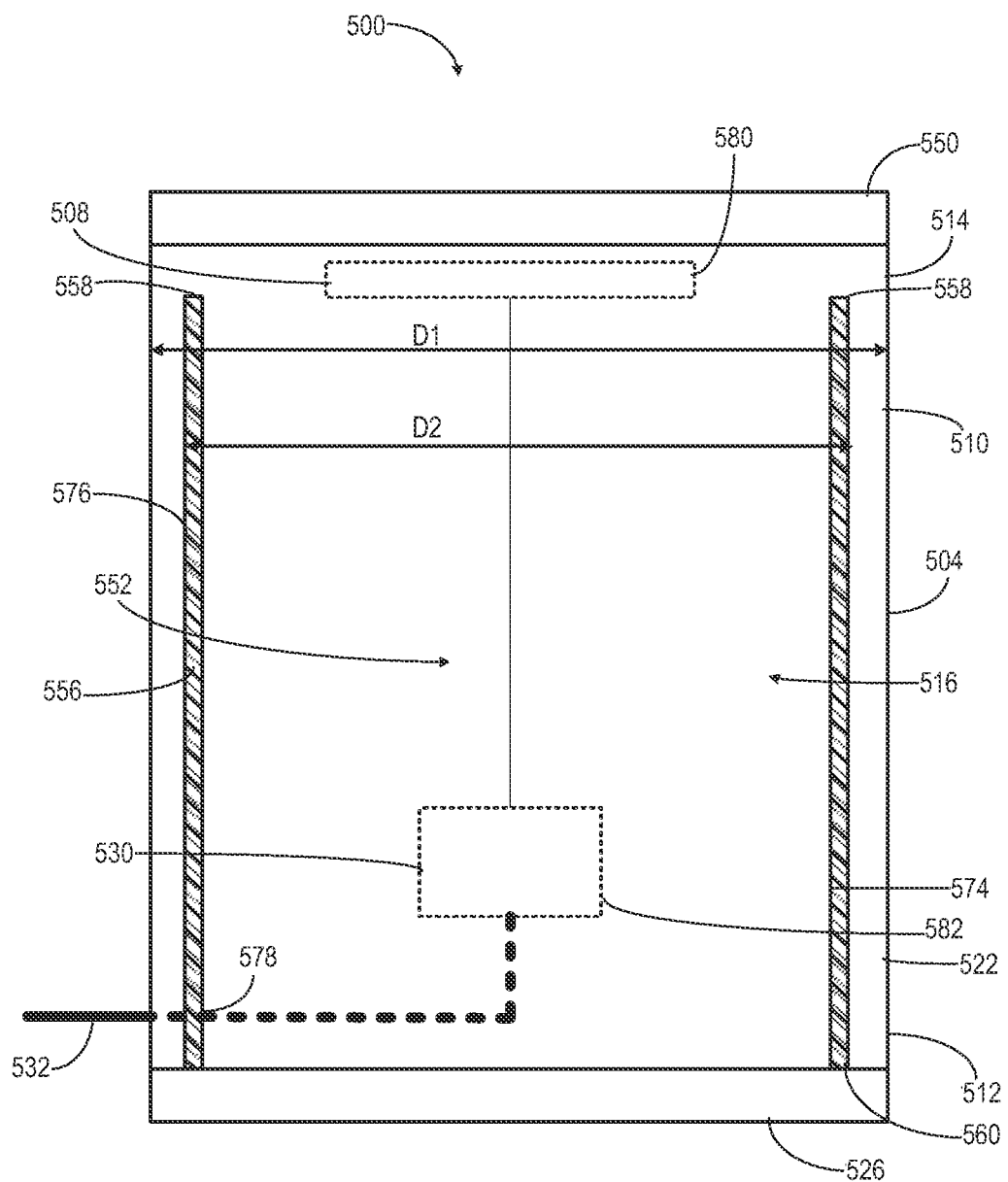
FIG. 34 is a cross-sectional view of the wax warmer taken generally along the line 34-34 of FIG. 29 with the electrical barrier in a third position.

As shown in FIG. 31, the top edge 558 of the electrical barrier 556 is in direct contact with the top plate 550, and the bottom edge 560 is in direct contact with the base plate 526. In an alternative embodiment, as shown in FIG. 33, the top edge 558 of the electrical barrier 556 is in direct contact with the top plate 550, and the bottom edge 560 is not in direct contact with the base plate 526, such that the electrical barrier 556 extends from the top plate 550 toward the bottom end 512 of the body 504. In yet another alternative embodiment, as shown in FIG. 34, the top edge 558 of the electrical barrier 556 is not in direct contact with the top plate 550, and the bottom edge 560 is in direct contact with the base plate 526, such that the electrical barrier 556 extends from the base plate 526 toward the top end 514 of the body 504. When either of the edges 558 and 560 are in direct contact with either of the plates 526 and 550, the connection can be made by a press fit, interference fit, integral molding or extrusion, or any other means providing for a substantially immovable fit as would be known to one of ordinary skill in the art.

Figure 35:
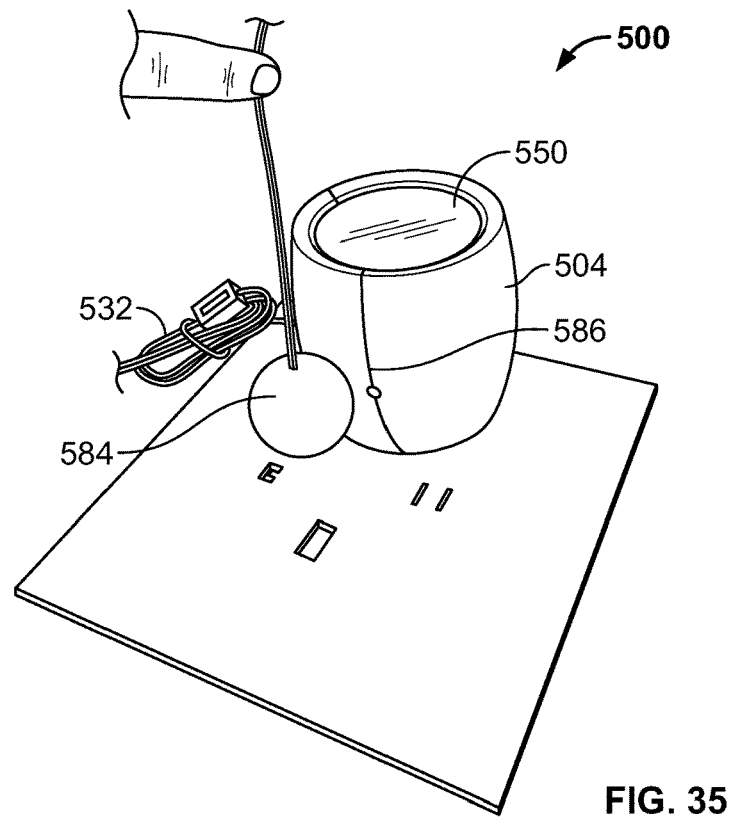
FIG. 35 is an image of a wax warmer undergoing a ball impact test.

Turning now to FIGS. 35 and 36, the embodiments of the wax warmer 500 are shown after a ball impact test is performed as required by the UL 283 standard for air fresheners and deodorizers. First, a steel ball 584 is configured to impact the body 504 of the wax warmer 500 from a specified distance of approximately 60 centimeters. The steel ball 584 may weigh approximately 535 grams and have a diameter of about 5.08 centimeters. As shown in FIG. 35, after the steel ball 584 engages the body 504, cracks 586 may form and the electrical assembly (not shown) is unexposed and inaccessible to a user's finger. As shown in FIG. 36, the body 504 has been removed from the wax warmer 500 after impact of the steel ball 584 and shows the electrical barrier 556 shielding the electrical assembly. Thus, the wax warmer 500 has passed the ball impact test according to the UL 283 standard. More specifically, although cracks 586 are present on the body 504, a finger probe (not shown) is incapable of contacting the electrical assembly 552 of the wax warmer 500 due to the presence of the electrical barrier 556. According to the UL 283 standard, if the finger probe can contact the electrical components through the broken ceramic housing, the wax warmer does not pass the ball impact test.

In contrast, conventional wax warmers typically fail the ball impact test since an electrical barrier is not present. Once the steel ball impacts a conventional wax warmer, the ceramic body breaks and the electrical components are exposed. A user and/or a finger probe can contact the live electrical components, making conventional wax warmers non-compliant with the UL 283 standard.

The wax warmer 500 in the embodiments depicted herein may be assembled quickly and efficiently. A wire harness (not shown) is first connected to the heater assembly 508, the electrical light source 530, and the electrical cord 532. It is contemplated that the electrical cord 532 may be replaced by batteries (not shown) contained within the body 504. It is further contemplated that any suitable electrical power source known to those having ordinary skill in the art may suffice. The next step in assembly is to insert the electrical assembly 552 (i.e., the heater assembly 508 and the electrical light source 530) into the interior space 516 of the body 504. Next, the electrical barrier 556/656 is inserted into the interior space 516 of the body 504 to surround the electrical assembly 552. Lastly the base plate 526 is attached to the bottom end 512 of the body 504.

FIG. 37 is a schematic of an example heating control circuit 700, which may be used to implement the heater assembly 108 of FIG. 1, the heater assembly 308 of FIG. 17, and/or the heating assembly 508 of FIG. 28 to melt a wax melt (e.g., the wax melt 102 of FIG. 1) in accordance with the teachings of this disclosure. In the illustrated example, the heating control circuit 700 is an electrical circuit that functions as a resistive type heater. In FIG. 37, the heating control circuit 700 is operatively coupled to a power source 702. The heating control circuit 700 of FIG. 37 includes a first resistor 704, a second resistor 706, a switch 708, and a temperature sensing device 710. The first resistor 704 and the second resistor 706 are connected in parallel. The second resistor 704 is connected in series with the switch 708 and the temperature sensing device 710. Thus, current supplied by the power source 702 to the heating control circuit 700 passes through the first resistor 704 via first electrical path 712 and through the second resistor 706, the switch 708, and the temperature sensing device 710 via a second electrical path 714.

Power (e.g., electrical current) generated by the power source 702 may be supplied via an electric current to the heating control circuit 700 by, for example, operatively coupling the heating control circuit 700 to the electrical outlet 112 via the power cord 110 of FIG. 1. In some examples, the power source 702 is one or more batteries, which may be housed in the wax warmer 100 of FIG. 1, the wax warmer 150 of FIG. 1A, the wax warmer 200 of FIG. 2, the wax warmer 300 of FIG. 15, the wax warmer 500 of FIG. 28, and/or any other wax warmer in accordance with the teachings of this disclosure. In other examples, the power source 702 is implemented in other ways. In some examples, the heating control circuit 700 includes a processor operatively coupled to the power source 702. The processor may include a timer or clock to enable the processor to schedule a supply of power to the heating control circuit 700 and/or control a duration of time during which the power source 702 supplies current to the heating control circuit 700. For example, the processor may control the supply of power to the heating control circuit 700 such that the heating control circuit 700 receives power for a predetermined time period (e.g., two hours, four hours, etc.) beginning at a predetermined time (e.g., eight o'clock p.m., 7 o'clock a.m., etc.). When the predetermined time period ends, the processor prevents the power source 702 from supplying power to the heating control circuit 700.

During operation of the heating control circuit 700 of FIG. 37, the power source 702 supplies current to the heating control circuit 700. As a result, the power source 702 may generate power of about 20 Watts. In some examples, the power source 702 initially supplies the current to the heating control circuit 700 when the power source 702 is operatively coupled to the heating control circuit 700 such as, for example, when the electrical cord 110 is inserted into and/or mated with the electrical outlet 112. In some examples, the power source 702 initially delivers current to the heating control circuit 700 upon actuation of a switch, in response to a controller communicating a signal to the power source 702, and/or in response to one or more additional events and/or conditions being met.

In the illustrated example, the first resistor 704 has an electrical resistance of about 720 ohms and has a power rating of about 20 Watts. In other examples, the first resistor 704 has other electrical resistances and/or power ratings. The second resistor 706 of FIG. 37 has an electrical resistance of about 720 ohms and a power rating of about 20 Watts. Thus, in the illustrated example, the first resistor 704 and the second resistor 706 have substantially the same electrical resistance. In other examples, the second resistor 706 has other electrical resistances and/or power ratings. In some examples, the first resistor 704 and the second resistor 706 have different electrical resistances.

The temperature sensing device 710 of FIG. 37 controls the switch 708 based on a temperature of the temperature sensing device 710, a temperature of the wax melt, and/or one or more additional and/or alternative temperatures of one or more additional and/or alternative components. In the illustrated example, the temperature sensing device 710 may be a bi-metal thermostat employing two or more materials (e.g., metals) having different thermal expansion coefficients. As a result, the temperature sensing device 710 of FIG. 37 deforms (e.g., bends) as a temperature of the temperature sensing device 710 increases and/or decreases. In such examples, the temperature sensing device 710 is operatively coupled to the switch 708 such that when the temperature sensing device 710 and/or the wax melt reaches a predetermined temperature and/or temperature range, deformation of the temperature sensing device 710 moves the switch 708 from a closed position to an open position. In some examples, when the wax melt is above about 70 degrees Celsius, the temperature sensing device moves the switch 708 to the open position. When the wax melt is below the predetermined temperature (e.g., below about 70 degrees Celsius) and/or temperature range (e.g., below about 70 degrees Celsius to about 75 degrees Celsius), the temperature sensing device 710 causes the switch 708 to be in the closed position. In other examples, the temperature sensing device 710 is implemented in other ways. For example, the temperature sensing device 710 may include an actuator operatively coupled to the switch 708 and a temperature sensor such as, for example, a thermocouple. In some examples, the temperature sensing device 710 is implemented using a timer and an actuator operatively coupled to the switch 708. The actuator may have a processor programmed to open the switch 708 after a predetermined amount of time that corresponds to the predetermined temperature and/or temperature range. When the switch 708 is in the closed position, the switch 708 enables current to flow through the second resistor 706. When the switch 708 is in the open position, the switch 708 prevents the current from flowing through the second resistor 706. The switch 708 of FIG. 37 is illustrated in the open position.

The heating control circuit 700 rapidly heats a wax melt (e.g., the wax melt 102 of FIG. 1, the wax melt 302 of FIG. 16, the wax melt 502 of FIG. 28, etc.) when the heating control circuit 700 is in a first heating state to melt the wax melt and enable a fragrance and/or other material in the wax melt to be released into a surrounding environment. The heating control circuit 700 enters the first heating state when current is supplied to the heating control circuit 700 and a temperature of the wax melt is below the predetermined temperature and/or temperature range. During the first heating state, the temperature sensing device 710 maintains the switch 708 in the closed position. As a result, the current passes through the first resistor 704 and the second resistor 706, and the first resistor 704 and the second resistor 706 generate heat. An amount of heat generated by the first resistor 704 and the second resistor 706 during the first heating state is a function of a first overall resistance of the heating control circuit 700.

In some examples, the heat increases a temperature of the wax melt from a first temperature below a melting point of the wax melt to a second temperature above the melting point of the wax melt in a predetermined amount of time. In some examples, the first temperature is substantially room temperature such as, for example, about 20 degrees Celsius to about 26 degrees Celsius. In other examples, the first temperature is other temperatures. In some examples, the second temperature is about 70 degrees Celsius to about 75 degrees Celsius. In other examples, the second temperature is other temperatures. In some embodiments, the heating control circuit 700 heats the wax melt from the first temperature to the second temperature in about 10 minutes to about 45 minutes. In some examples, the heating control circuit 700 heats the wax melt from the first temperature to the second temperature in about 10 minutes to about 25 minutes.

Once the wax melt reaches the second temperature, the heating control circuit 700 enters a second heating state in which the heating control circuit 700 substantially maintains the wax melt within a temperature range above the melting point of the wax melt (e.g., at or near the second temperature). For example, when the wax melt reaches and/or exceeds the second temperature, the temperature sensing device 710 moves the switch 708 into the open position. As a result, the current does not flow through the second resistor 706 and, thus, the current only flows through the first resistor 704. Therefore, the heating control circuit 700 in the second heating state has a second overall resistance corresponding to a resistance of the first resistor 704. The second overall resistance of the heating control circuit 700 in the second heating state is greater than the first overall resistance when the heating control circuit 700 is in the first heating state. As a result, a second amount of heat generated by the heating control circuit 700 in the second heating state is less than a first amount of heat generated by the heating control circuit 700 in the first heating state. The second amount of heat, which is generated from substantially only the first resistor 704, maintains the wax melt temperature substantially at the second temperature to enable the wax melt to consistently release a desired amount of fragrance and/or other material contained therein into a surrounding environment. In some examples, the heating control circuit 700 maintains the temperature of the wax melt between about 70 degrees Celsius to about 75 degrees Celsius when the heating control circuit 700 is in the second heating state.

Figure 15:
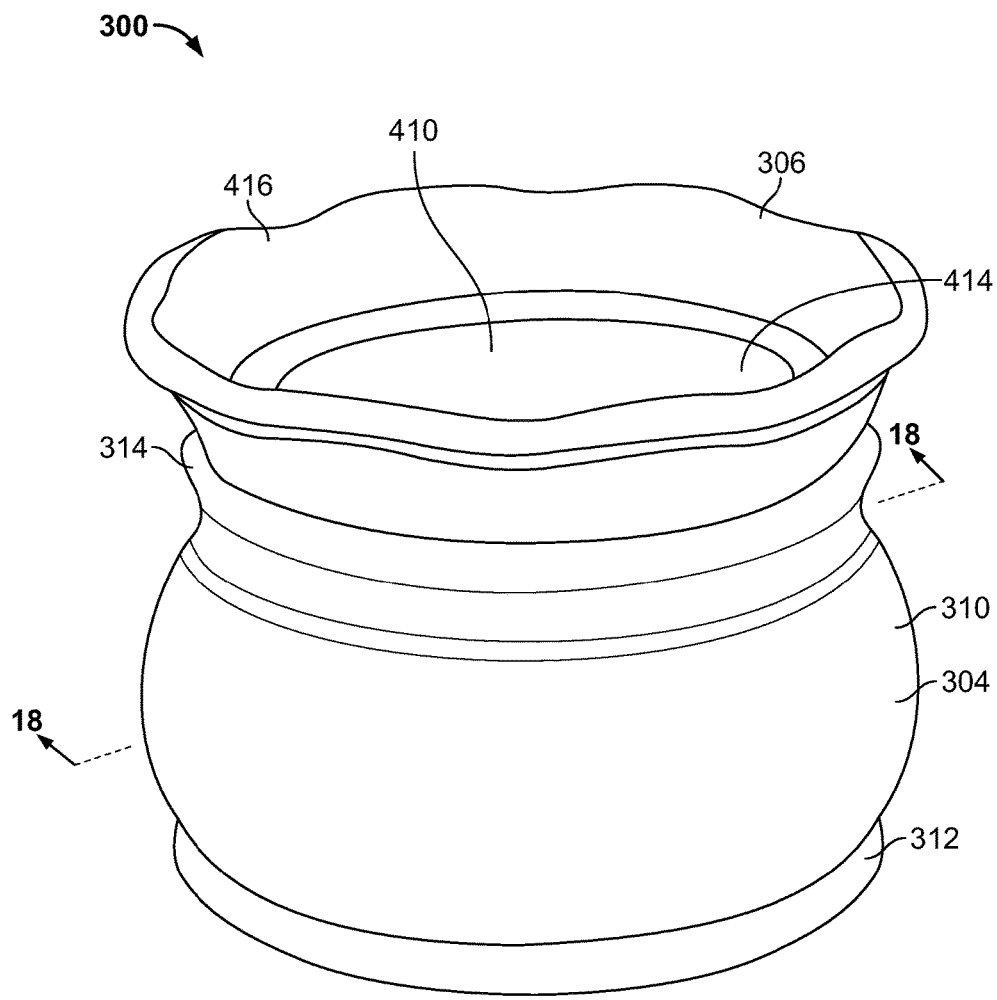
FIG. 15 is a perspective view of another wax warmer.
Figure 16:
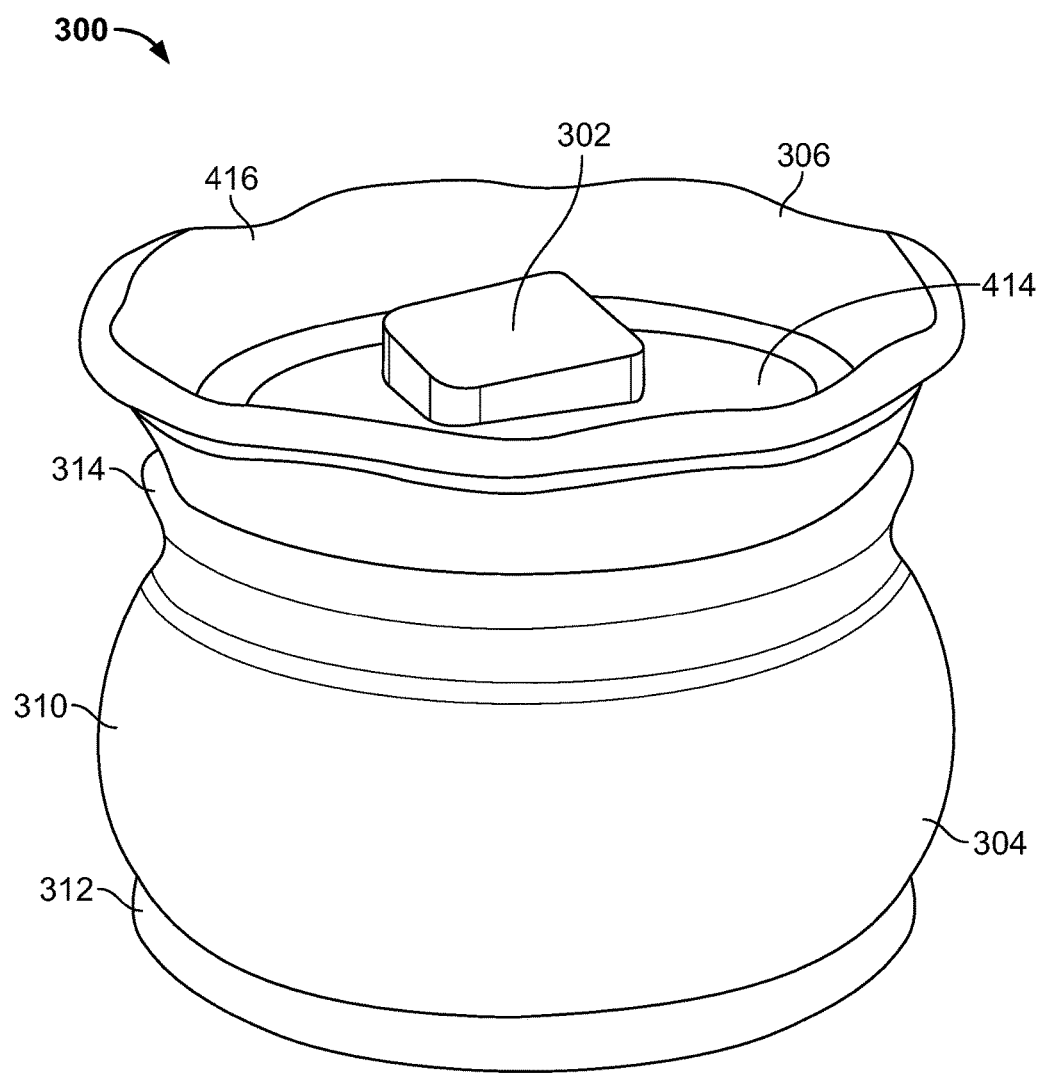
FIG. 16 is a perspective view of the wax warmer of FIG. 15 with a wax melt.

As discussed above, the heating control circuit 700 may be employed by the wax warmer 100 of FIG. 1, the wax warmer 150 of FIG. 1A, the wax warmer 300 of FIG. 15, and/or the wax warmer 500 of FIG. 28. In such examples, the heating control circuit 700 controls the heat generated via the first resistor 704 and the second resistor 706 such that a temperature of the body 104 of FIGS. 1 and 1A, and the body 304 of FIG. 15, and the body 504 of FIG. 28, respectively, does not exceed a temperature of about 65 degrees Celsius when the heating control circuit 700 is in the first heating state and/or when the heating control circuit 700 is in the second heating state.

Now turning to FIG. 38, a schematic of another example heating control circuit 750 is disclosed herein. The heating control circuit 750 of FIG. 38 may be used to implement the heater assembly 108 of FIG. 1, the heater assembly 308 of FIG. 17, and/or the heating assembly 508 of FIG. 28 to melt a wax melt (e.g., the wax melt 102 of FIG. 1) in accordance with the teachings of this disclosure. In the illustrated example, the heating control circuit 750 is a resistive type heater. In FIG. 38, the heating control circuit 750 is operatively coupled to a power source 752. The heating control circuit 750 of FIG. 38 includes a first resistor 754, a second resistor 756, a third resistor 758, a first switch 760, a second switch 762, a first temperature sensing device 764, and a second temperature sensing device 766. The first resistor 754, the second resistor 756, and the third resistor 758 are connected in parallel. The second resistor 756 is connected in series with the first switch 760 and the first temperature sensing device 764. The third resistor 758 is connected in series with the second switch 762 and the second temperature sensing device 766. Thus, when current is supplied to the heating control circuit 750 of FIG. 38 and the first switch 760 and the second switch 762 are in a closed position, the current passes through the first resistor 754 via a first path 768; the current passes through the second resistor 756, the first switch 760 and the first temperature sensing device 764 via a second path 770; and the current passes through the third resistor 758, the second switch 762 and the second temperature sensing device 766 via a third path 772.

During operation, the power source 752 supplies electrical current to the heating control circuit 750. In some examples, the power source 752 generates about 20 Watts of power. In the illustrated example, the power source 752 initially supplies the current to the heating control circuit 750 when the power source 752 is operatively coupled to the heating control circuit 750 such as, for example, when an electrical cord (e.g., the electrical cord 110 of FIG. 1) is inserted into a household electrical outlet (e.g., the electrical outlet 112 of FIG. 1). In some examples, the power source 752 initially delivers current to the heating control circuit 750 upon actuation of a switch, in response to a controller communicating a signal to the power source 752, and/or in response to one or more additional events and/or conditions being met. In some examples, heating control circuit 750 includes a processor operatively coupled to the power source 752. The processor may include a timer or clock to enable the processor to schedule a supply of power to the heating control circuit 750 and/or control a duration of time during which the power source 752 supplies current to the heating control circuit 750. For example, the processor may control the supply of power to the heating control circuit 750 such that the heating control circuit 750 receives power for a predetermined time period (e.g., two hours, four hours, etc.) beginning at a predetermined time (e.g., eight o'clock p.m., 7 o'clock a.m., etc.). When the predetermined time period ends, the processor prevents the power source 752 from supplying power to the heating control circuit 750.

In the illustrated example, the first resistor 754 has a first electrical resistance of about of about 720 ohms. In other examples, the first resistor 754 has other electrical resistances. The second resistor 756 of FIG. 38 has a second electrical resistance of about 180 ohms to about 720 ohms. In other examples, the second resistor 756 has other electrical resistances. The third resistor 758 of FIG. 38 has a third electrical resistance of about 180 ohms to about 720 ohms. In other examples, the third resistor 758 has other electrical resistances. Thus, in the illustrated example, when the first switch 760 and the second switch 762 are in the closed position, the heating control circuit 750 has a first overall resistance.

In the illustrated example, the first temperature sensing device 764 and the second temperature sensing device 766 are each substantially similar or identical to the temperature sensing device 710 of FIG. 37. The first temperature sensing device 764 of FIG. 38 is operatively coupled to the first switch 760 to control actuation of the first switch 760 based on a temperature of the first temperature sensing device 764, a temperature of the wax melt, and/or one or more additional and/or alternative temperatures of other components. The second temperature sensing device 766 of FIG. 38 is operatively coupled to the second switch 762 to control actuation of the second switch 762 based on a temperature of the second temperature sensing device 766, a temperature of the wax melt, and/or one or more additional and/or alternative temperatures of other components. For example, when the wax melt is below a first predetermined temperature (e.g., about 70 degrees Celsius), the first temperature sensing device 764 causes the first switch 760 to be in a closed position. In some embodiments, when the wax melt is below a second predetermined temperature, the second temperature sensing device 766 causes the second switch 762 to be a closed position. In some examples, the first predetermined temperature and the second predetermined temperature are substantially the same. In other examples, the first predetermined temperature and the second predetermined temperature are different. When the first switch 760 is in the closed position, the first switch 760 enables current to flow through the second resistor 756. When the second switch 762 is in the closed position, the second switch 762 enables the current to flow through the third resistor 758. The first switch 760 and the second switch 762 of FIG. 38 are illustrated in the open position.

In some examples, when the wax melt reaches and/or exceeds the first predetermined temperature, the first temperature sensing device 764 moves the first switch 760 from the closed position to an open position. When the wax melt reaches the second predetermined temperature, the second temperature sensing device 766 moves the second switch 762 from the closed position to an open position. When the first switch 760 is in the open position, the current does not flow through the second resistor 756. When the second switch 762 is in the open position, the current does not flow through the third resistor 758. As a result, substantially all of the current flows through the first resistor 754 when the heating control circuit 750 is in the second heating state, and the heating control circuit 750 has a second overall resistance greater than the first overall resistance.

The heating control circuit 750 has a first heating state in which the heating control circuit 750 rapidly heats the wax melt to enable the wax melt to release a fragrance and/or material(s) into a surrounding environment. The heating control circuit 750 enters the first heating state when current is supplied to the heating control circuit 750 and the temperature of the wax melt is below the first predetermined temperature and/or the second predetermined temperature. During the first heating state, the first temperature sensing device 764 and the second temperature sensing device 766 maintain the first switch 760 and the second switch 762, respectively, in the closed position. When power is delivered to the heating control circuit 750, the first switch 760 is in the closed position, the second switch 762 is in the closed position, and the heating control circuit 750 generates heat via the first resistor 754, the second resistor 756, and the third resistor 758. An amount of heat generated by the first resistor 754, the second resistor 756, and the third resistor 758 is a function of a second overall resistance of the first resistor 754, the second resistor 756, and the third resistor 758.

In some examples, the heat rapidly and efficiently increases a temperature of the wax melt from a first temperature below a melting point of the wax melt to a second temperature above the melting point of the wax melt. For example, the heating control circuit 750 may heat the wax melt from the first temperature to the second temperature in about 10 minutes to about 45 minutes. In some examples, the heating control circuit 750 heats the wax melt from the first temperature to the second temperature in about 10 minutes to about 25 minutes. In some examples, the first temperature is substantially room temperature such as, for example, about 20 degrees Celsius to about 26 degrees Celsius. In other examples, the first temperature is other temperatures. In some examples, the second temperature is about 70 degrees Celsius to about 75 degrees Celsius. In other examples, the second temperature is other temperatures.

Once the wax melt reaches the second temperature, the heating control circuit 750 enters a second heating state in which the heating control circuit 750 substantially maintains the wax melt at or near the second temperature. For example, when the wax melt reaches the second temperature, the first temperature sensing device 764 moves the first switch 760 from the closed position to the open position, and the second temperature sensing device 766 moves the second switch 762 from the closed position to the open position. In other examples, when the wax melt reaches the second temperature, only one of the first switch 760 or the second switch 762 is opened. When the first switch 760 and the second switch 762 are in the open position, the current does not flow through the second resistor 756 or the third resistor 758, respectively. As a result, the current flows through substantially only the first resistor 754. Therefore, the heating control circuit 750 in the second heating state has a second overall resistance corresponding to the resistance of the first resistor 754. Thus, a second amount of heat generated by the heating control circuit 750 in the second heating state is less than a first amount of heat generated by the heating control circuit 700 in the first heating state. In the illustrated example, the second amount of heat generated by the heating control circuit 750 substantially maintains the temperature of the wax melt at the second temperature to enable the wax melt to consistently release a desired amount of fragrance or other material contained therein into a surrounding environment. In some examples, the heating control circuit 750 maintains the temperature of the wax melt between about 70 degrees Celsius to about 75 degrees Celsius when the heating control circuit 750 is in the second heating state.

As discussed above, the heating control circuit 750 may be employed by the wax warmer 100 of FIG. 1, the wax warmer 150 of FIG. 1A, the wax warmer 300 of FIG. 15, and the wax warmer 500 of FIG. 28. In such examples, the heating control circuit 750 controls a temperature generated via the first resistor 754, the second resistor 756, and the third resistor 758 such that a temperature of the body 104 of FIG. 1, and the body 304 of FIG. 15, and the body 504 of FIG. 28, respectively, does not exceed a temperature of about 65 degrees Celsius when the heating control circuit 750 is in the first heating state and/or when the heating control circuit 750 is in the second heating state.

Figure 39:
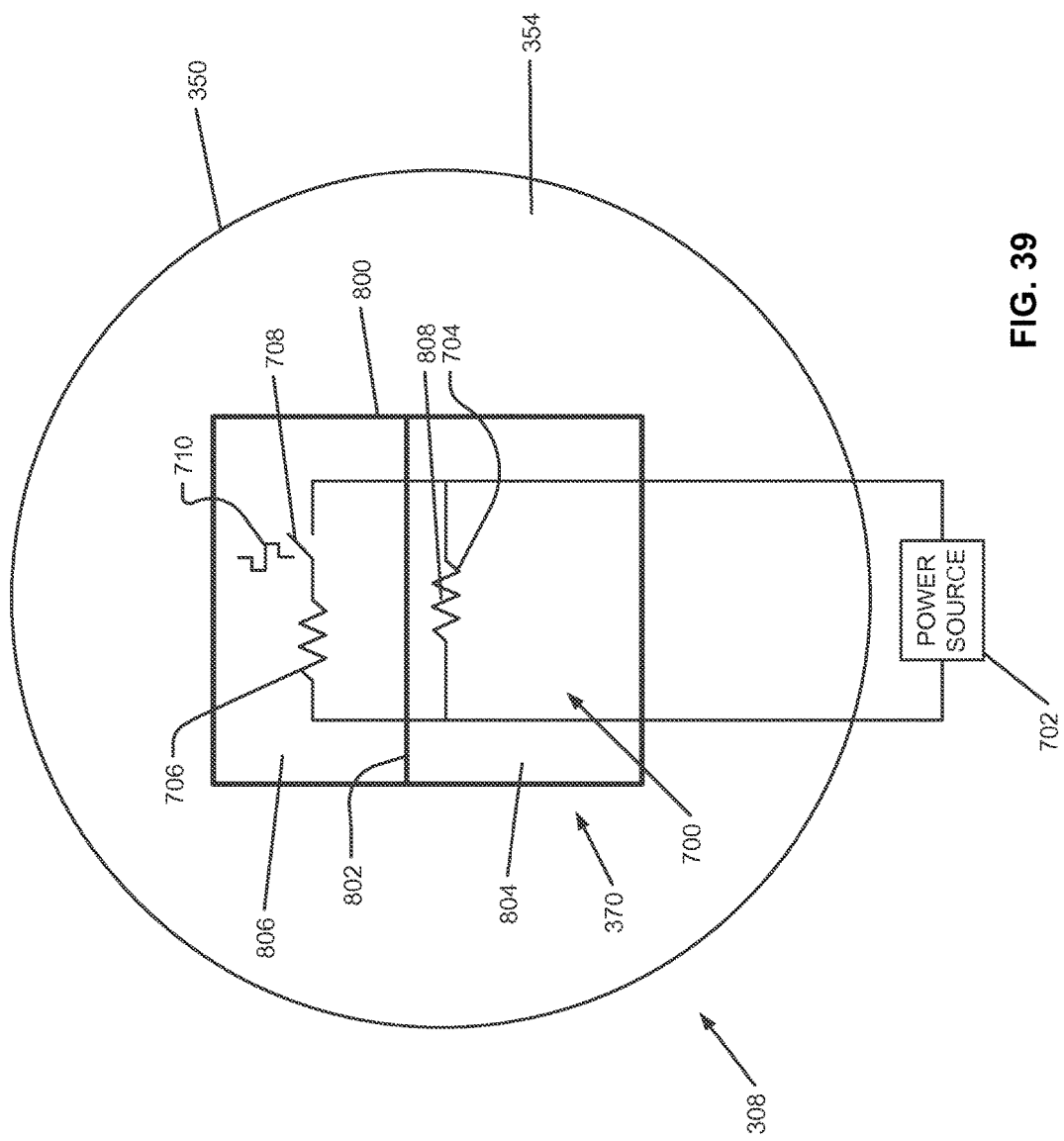
FIG. 39 is a schematic depiction of the wax warmer of FIG. 17 employing the heating control circuit of FIG. 37.

FIG. 39 illustrates the heater assembly 308 of FIG. 17 employing the heating control circuit 700 of FIG. 37. Although the following examples are described in conjunction with the heater assembly 308 of FIG. 17, the heater assembly 108 of FIG. 1 and/or the heating assembly 508 of FIG. 28 may employ the example heating control circuit 700.

The heater 370 is operatively coupled to the second surface 354 of the plate 350 to enable heat from the heater 370 to be transferred to the wax melt 302. In the illustrated example, the heater 370 includes a housing 800. The housing 800 includes a barrier 802 disposed inside the housing 800 to define a first compartment 804 and a second compartment 806. Other examples may include other numbers of barriers (e.g., 2, 3, 4, etc.) and/or compartments (e.g., 1, 2, 3, 4, 5, 6, 7, etc.).

The first resistor 704 of the heating control circuit 700 of FIG. 37 is disposed in the first compartment 804 of the housing 800. The second resistor 706, the switch 708, and the temperature sensing device 710 are disposed within the second compartment 806 of the housing 800. The first compartment 804 and the second compartment 806 are each substantially filled with electrical insulation (e.g., silicone) to protect and/or insulate the first resistor 704 and the second resistor 706. In some examples, the first compartment 804 and the second compartment 806 are substantially the same size (e.g., internal volume). In other examples, the first compartment 804 and the second compartment 806 are different sizes. In some embodiments, the housing 800 is positioned on the plate 350 such that a portion of the housing 800 and/or the first resistor 704 is substantially on a center 808 of the second surface 354 of the plate 350 to enable a substantially even or balanced radial distribution of heat via the plate 350 when the heating control circuit 700 is in the first heating state and/or the second heating state. In other examples, the first resistor 704 is radially spaced apart from the center 808 of the second surface 354 of the plate 350. Although not shown in FIG. 39, the heater assembly 308 may include a second plate (e.g., the second plate 856 of FIG. 40) coupled to the plate 350 to facilitate radial heat distribution via the plate 350.

Figure 40:
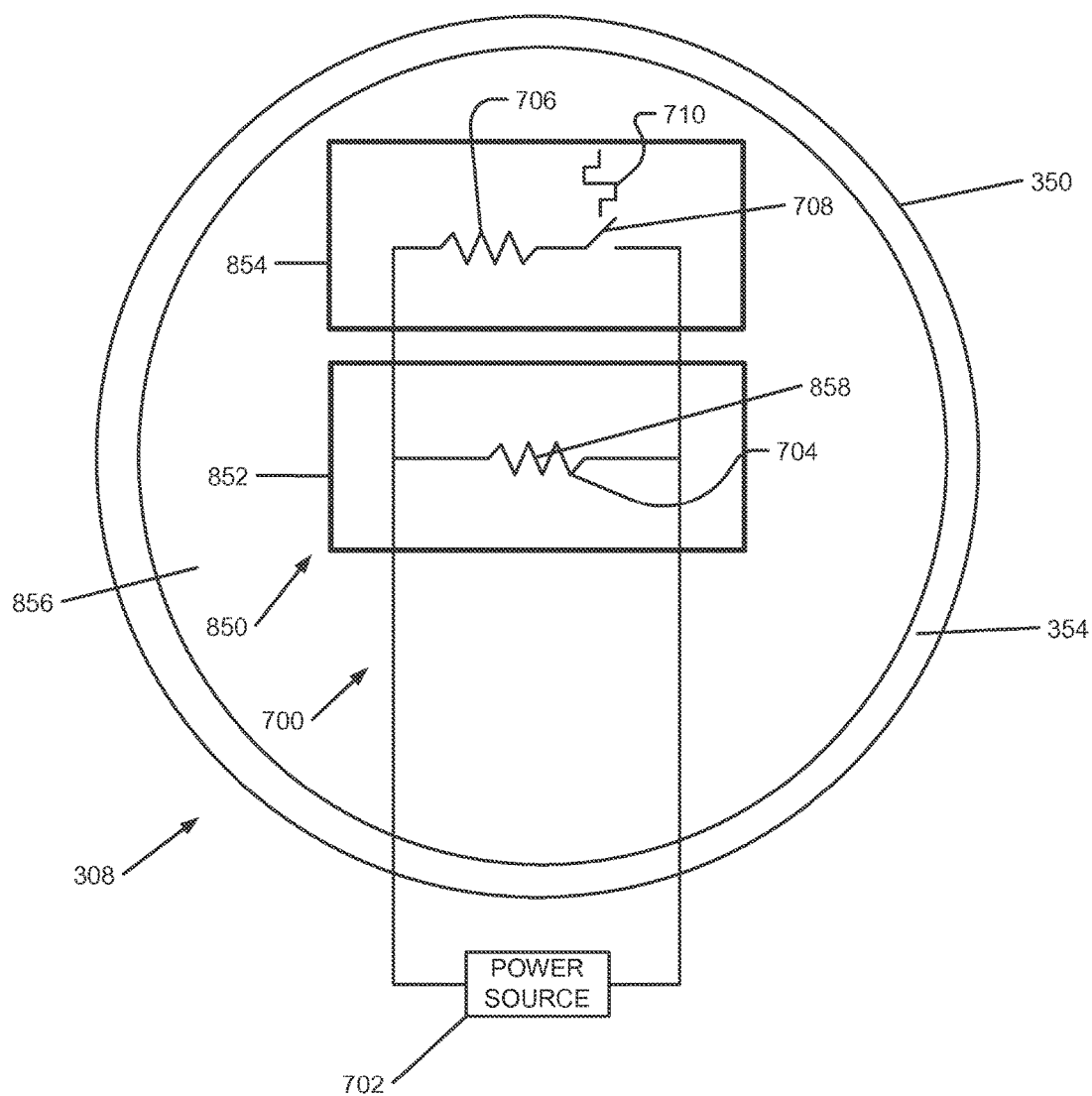
FIG. 40 is a different schematic depiction of the wax warmer of FIG. 17 employing the heating control circuit of FIG. 37.

FIG. 40 illustrates the heater assembly 308 employing another example heater 850 disclosed herein. Although the following examples are described in conjunction with the heater assembly 308, the example heater 850 may be used to implement the heater assembly 108 of FIG. 1 and/or the heating assembly 508 of FIG. 28. In the illustrated example, the heater 850 includes a first housing 852 and a second housing 854. The first housing 852 and the second housing 854 are operatively coupled to the second surface 354 of the plate 350. In the illustrated example, the first housing 852 is spaced apart from the second housing 854. In other examples, the first housing 852 is not spaced apart from the second housing 854. For example, the first housing 852 may abut or contact the second housing 854.

The heater 850 of FIG. 40 employs the heating control circuit 700 of FIG. 37. The first resistor 704 of the heating control circuit 700 is disposed within the first housing 852. The second resistor 706, the switch 708, and the temperature sensing device 710 of the heating control circuit 700 are disposed within the second housing 854. The first housing 852 and the second housing 854 are each filled with electrical insulation (e.g., silicone) to protect and/or insulate the first resistor 704 and the second resistor 706, respectively.

In the illustrated example, the plate 350 is a first plate, and the heater assembly 308 includes a second plate 856. A first side of the second plate 856 is coupled to the first plate 350. The first housing 852 and the second housing 854 are coupled to a second side of the second plate 856 opposite the first side. In some examples, the second plate 856 has a greater heat transfer coefficient than the first plate 350 to facilitate dispersion of heat generated by the first resistor 704 and the second resistor 706. For example, the first plate 350 may be ceramic and the second plate 856 may be aluminum. In other examples, the first plate 350 and/or the second plate 856 are one or more additional and/or alternative materials. In some examples, the heater assembly 308 does not include the second plate 856.

In FIG. 40, the first housing 852 is positioned on the heater assembly 308 such that a portion of the first housing 852 and/or the first resistor 704 is substantially on a center 858 of the first plate 350 and/or the second plate 856. In other examples, the first housing 852 and/or the first resistor 704 are positioned in other ways. In the illustrated example, the second housing 854 and the second resistor 706 are radially spaced apart from the center 858 of the first plate 350 and/or the second plate 856. In other examples, the second housing 854 and/or the second resistor 706 are positioned in other ways.

Figure 41:
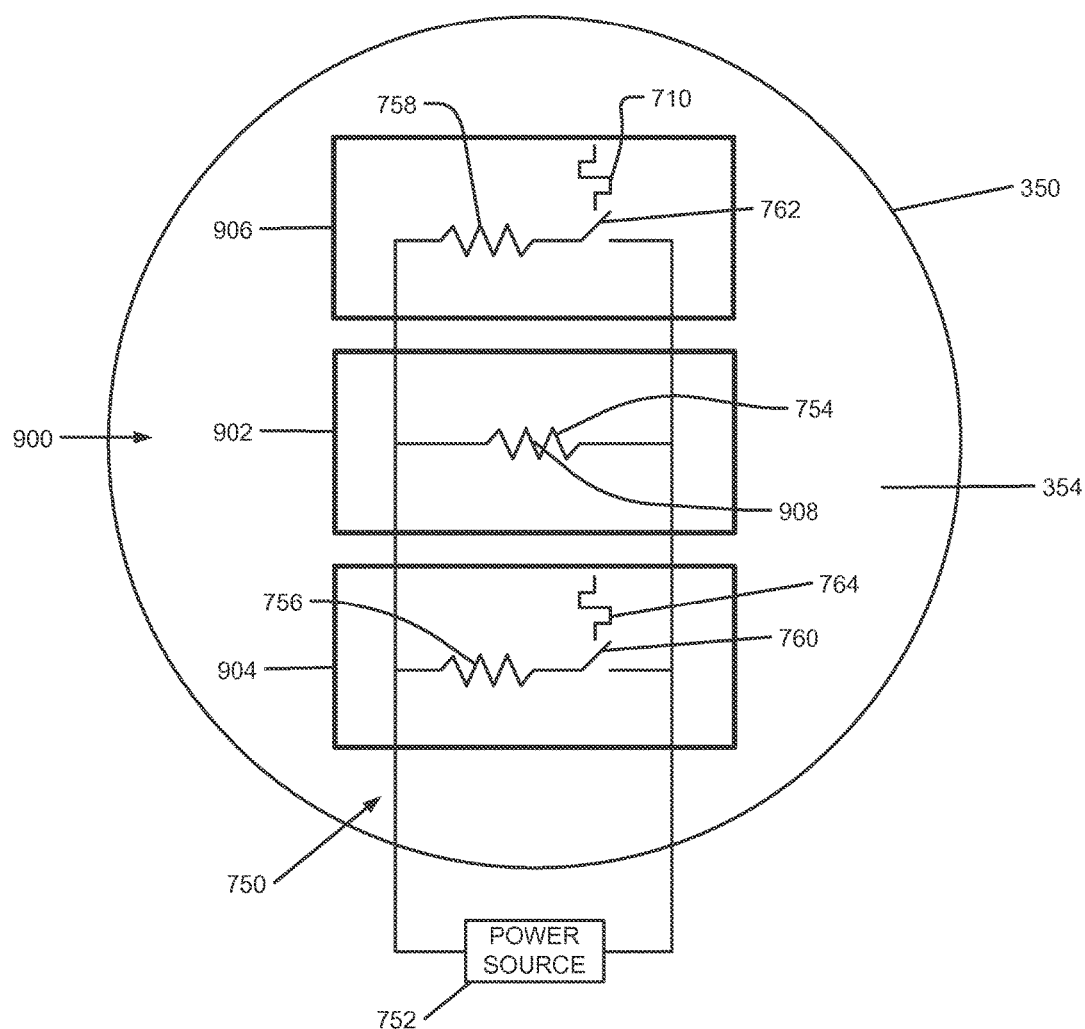
FIG. 41 is another schematic depiction of the wax warmer of FIG. 17 employing a heater of FIG. 38.

FIG. 41 illustrates the heater assembly 308 employing another example heater 900 disclosed herein. Although the following examples are described in conjunction with the heater assembly 308, the heater assembly 108 of FIG. 1 and/or the heating assembly 508 of FIG. 28 may employ the example heater 900 of FIG. 41. In the illustrated example, the heater 900 employs the heating control circuit 750 of FIG. 38. For example, the heater 900 includes a first housing 902, a second housing 904, and a third housing 906. The first housing 902, the second housing 904, and the third housing 906 are operatively coupled to the second surface 354 of a plate 350. In the illustrated example, the first housing 902, the second housing 904, and the third housing 906 are spaced apart. In other examples, two or more of the first housing 902, the second housing 904, and the third housing 906 abut and/or are in contact.

The first resistor 754 of the heating control circuit 750 of FIG. 38 is disposed within the first housing 902. The second resistor 756, the first switch 760, and the first temperature sensing device 764 of the heating control circuit 750 are disposed within the second housing 904. The third resistor 758, the second switch 762, and the second temperature sensing device 766 of the heating control circuit 750 are disposed within the third housing 906. The first housing 902, the second housing 904, and the third housing 906 are each substantially filled with electrical insulation (e.g., silicone) to protect and/or insulate the first resistor 754, the second resistor 756, and the third resistor 758. In some examples, the heater 900 has other numbers of housings. For example, the heater 900 may have one housing defining three compartments in which the first resistor 754, the second resistor 756, and the third resistor 758 are disposed, respectively.

In FIG. 41, a portion of the first housing 902 and/or a portion of the first resistor 754 is substantially on a center 908 of the plate 350. Thus, the second housing 904, the second resistor 756, the third housing 906, and the third resistor 758 are spaced apart from the center 908 of the plate 350. Further, the first housing 902, the second housing 904, and the third housing 906 are positioned in a row along a diameter of the plate 350. In other examples, the first housing 902, the second housing 904, and the third housing 906 are positioned in other ways.

As described above in conjunction with FIG. 38, in some examples, when the heating control circuit 750 is in the first heating state, the first resistor 754, the second resistor 756, and the third resistor 758 generate heat to rapidly or quickly heat the wax melt 302 to about 70 degrees Celsius to about 75 degrees Celsius. Once the wax melt 302 reaches or exceeds about 70 degrees Celsius, the first temperature sensing device 764 and the second temperature sensing device 766 open the first switch 760 and the second switch 762, respectively. As a result, the heating control circuit 750 enters the second heating state and employs substantially only the first resistor 754 to maintain the temperature of the wax melt 302 between about 70 degrees to about 75 degrees. In the illustrated example, because the first resistor 754 is substantially centered on the plate 350, radial heat distribution via the plate 350 is substantially even or balanced.

Figure 42:
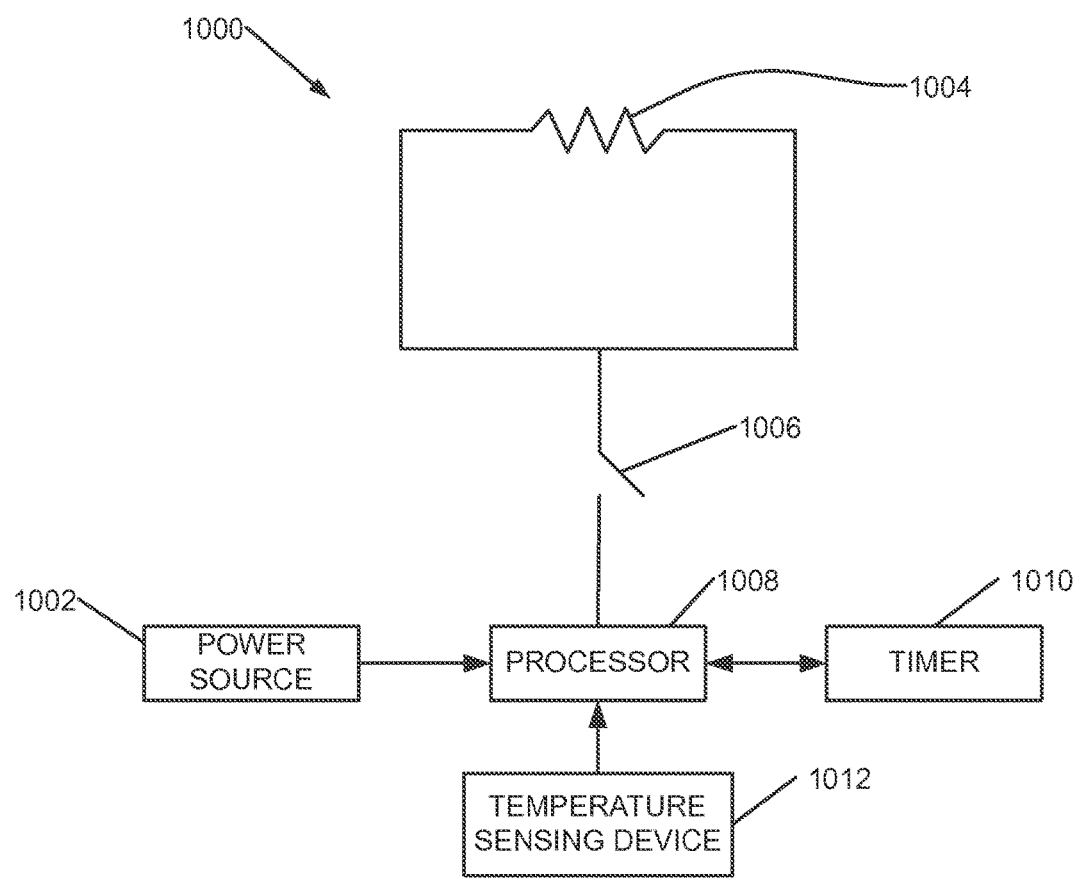
FIG. 42 is a schematic depiction of yet another heating control circuit disclosed herein, which may be used to implement the wax warmers of FIGS. 1-36.

FIG. 42 is a schematic of another example of a heating control circuit 1000 disclosed herein, which may be used to implement the heater assembly 108 of FIG. 1, the heater assembly 308 of FIG. 17, and/or the heating assembly 508 of FIG. 28 to melt a wax melt (e.g., the wax melt 102 of FIG. 1) in accordance with the teachings of this disclosure. In FIG. 42, the heating control circuit 1000 is operatively coupled to a power source 1002. The power source 1002 may be substantially similar or identical to the power source 702 of FIG. 37 and/or the power source 752 of FIG. 38. The heating control circuit 1000 of FIG. 42 includes a resistor 1004, a switch 1006, a processor 1008, a timer 1010, and a temperature sensing device 1012.

During operation of the heating control circuit 1000, the power source 1002 delivers power to the heating control circuit 1000. In some examples, during operation, the power source 1002 may deliver power having a range of about 20 Watts to about 50 Watts.

In the illustrated example, the resistor 1004 has a resistance of about 360 ohms and a power rating of about 40 Watts. In other examples, the resistor 1004 has other resistances and/or other power ratings. When the switch 1006 is in a closed position, the current from the power source 1002 flows through the resistor 1004 and, thus, the resistor 1004 generates heat. When the switch 1006 is in an open position, the switch does not permit the current to flow through the resistor 1004. The temperature sensing device 1012 determines a temperature of the wax melt, the heating control circuit 1000 and/or one or more additional and/or alternative components of a heating assembly employed to melt the wax melt. In some examples, the temperature sensing device 1012 is a thermostat, a temperature sensor, a thermocouple, and/or one or more additional and/or alternative types of temperature sensing devices.

The processor 1008 controls the switch 1006. In the illustrated example, the processor 1008 employs a first heating state in which the processor 1008 maintains the switch 1006 in the closed position to rapidly melt the wax melt. Thus, in the illustrated example, the processor 1008 enters the first heating state if power is supplied to the heating control circuit 1008 and the temperature sensing device 1012 determines that a temperature of the wax melt is below a predetermined temperature such as, for example, 70 degrees Celsius. When the heating control circuit 1000 is in the first heating state, the resistor 1004 generates a first amount of heat. As a result, in some embodiments, the heating control circuit 1000 heats the wax melt from substantially room temperature to between about 70 degrees Celsius to about 75 degrees Celsius in about 10 minutes to about 45 minutes. In some examples, the heating control circuit 1000 heats the wax melt from substantially room temperature to between about 70 degrees Celsius to about 75 degrees Celsius in about 10 minutes to about 25 minutes when the heating control circuit 1000 is in the first heating state.

The processor 1008 employs a second heating state when the temperature of the wax melt reaches and/or exceeds the predetermined temperature. In some examples, the processor 1008 employs pulse-width modulation during the second heating state to supply pulses of current to the resistor 1004 at a predetermined frequency by controlling the switch 1006. For example, the processor 1008 may cycle the switch 1006 between an open position and a closed position to supply current to the resistor 1004 during spaced apart intervals of time. The processor 1008 employs the timer 1010 to control durations of the pulses of current supplied to the resistor 1004 and, thus, a second amount of heat generated by the resistor 1004. In some examples, the timer 1010 is an auto shut-off timer. When the processor 1008 is in the second heating state, the second amount of heat generated by the resistor 1004 is less than the first amount of heat. As a result, the heat generated via the heating control circuit 1000 in the second heating state substantially maintains the wax melt at a temperature between about 70 degrees Celsius to about 75 degrees Celsius. In some embodiments, the processor 1008 employs pulse-width modulation during the first heating state. In such embodiments, the pulses of current supplied to the resistor 1004 may be longer and/or spaced apart by shorter amounts of time than the pulses employed during the second heating state.

Any of the embodiments described herein may be modified to include any of the structures or methodologies disclosed in connection with different embodiments. Further, the present disclosure is not limited to wax warmers of the type specifically shown. Still further, the wax warmers of any of the embodiments disclosed herein may be modified to work with any type of warmer that utilizes wax melts or the like.

What is claimed is:

1. A wax warmer, comprising:
a body to support a reservoir adapted to receive a wax melt; and
an electrical circuit operatively coupled to the body to heat the wax melt from a first temperature below a melting point of the wax melt to a second temperature above the melting point of the wax melt, the electrical circuit having a first heating state and a second heating state, the electrical circuit in the first heating state having a first overall resistance, the electrical circuit in the second heating state having a second overall resistance greater than the first electrical resistance;
wherein the electrical circuit comprises a first resistor and a second resistor; and
wherein the first resistor is disposed in a first compartment of the housing, and the second resistor is disposed in a second compartment of the housing, the first and second compartments being defined by a barrier disposed therebetween to insulate the first resistor from the second resistor.

2. The wax warmer of claim 1, wherein the first resistor and the second resistor are connected in parallel.

3. The wax warmer of claim 2 further comprising a switch connected in series with the second resistor.

4. The wax warmer of claim 3 further comprising a temperature sensing device connected in series with the second resistor, the temperature sensing device to control the switch.

5. The wax warmer of claim 4, wherein the temperature sensing device comprises a bi-metal thermostat operatively coupled to the switch.

6. The wax warmer of claim 4, wherein the temperature sensing device comprises an actuator and a temperature sensor, the actuator operatively coupled to the switch.

7. The wax warmer of claim 4, wherein the temperature sensing device comprises an actuator and a timer, the actuator operatively coupled to the switch.

8. The wax warmer of claim 1 further comprising a first plate to support the reservoir on the body, the first plate interposing the heater and the reservoir.

9. The wax warmer of claim 8, further comprising a second plate having a first side and a second side opposite the first side, the first plate coupled to the first side, the electrical circuit coupled to the second side, wherein the second plate has a greater heat transfer coefficient than the first plate.

10. The wax warmer of claim 1, wherein the electrical circuit comprises a switch and a temperature sensing device to control the switch, wherein the electrical circuit is to be in the first heating state when the switch is in a closed position, and wherein the electrical circuit is to be in the second heating state when the switch is in an open position.

11. The wax warmer of claim 10, wherein the first resistor and the second resistor are connected in parallel, and wherein the temperature sensing device, the switch, and the second resistor are connected in series.

12. The wax warmer of claim 11, wherein the electrical circuit comprises:
a second switch;
a second temperature sensing device to control the second switch; and
a third resistor connected in parallel with the first resistor and the second resistor, the third resistor connected in series with the second switch and the second temperature sensing device.

13. A wax warmer, comprising:
a body to support a reservoir adapted to receive a wax melt;
a heater including a first resistor and a second resistor, the heater having a first heating state to heat the wax melt from a first temperature below a melting point of the wax melt to a second temperature above the melting point of the wax melt in a predetermined amount of time, the heater having a second heating state with a greater overall resistance than the first heating state to substantially maintain the wax melt within a temperature range above the melting point of the wax melt;
wherein the first resistor is disposed in a first housing, and the second resistor is disposed in a second housing; and
wherein the first and second housings are substantially filled with insulation.

14. The wax warmer of claim 13, wherein the first temperature is about room temperature, the second temperature is between about 70 degrees Celsius to about 75 degrees Celsius, and the predetermined amount of time is between about 10 minutes to about 25 minutes.

15. The wax warmer of claim 13 further comprising a processor including a timer, the processor to control a duration of time during which the heater is to receive power from a power supply.

16. The wax warmer of claim 13, wherein the heater comprises:
the second resistor connected in parallel with the first resistor;
a switch connected in series with the second resistor; and
a thermostat to control the switch.

17. The wax warmer of claim 13, wherein the heater comprises:
a switch connected in series with one of the first or second resistors; and
a processor to control the switch to employ pulse-width modulation to control an amount of heat generated by the resistor.

18. The wax warmer of claim 13, wherein a first plate interposes the heater and the reservoir.

19. The wax warmer of claim 18 further comprising a second plate having a first side and a second side opposite the first side, the first plate coupled to the first side, the heater coupled to the second side, wherein the second plate has a greater heat transfer coefficient than the first plate.

* * * * *